United States Patent
Anwar et al.

(10) Patent No.: US 9,820,653 B2
(45) Date of Patent: Nov. 21, 2017

(54) METHODS, SYSTEMS, AND DEVICES FOR IMAGING MICROSCOPIC TUMORS

(71) Applicant: Regents of the University of California, Oakland, CA (US)

(72) Inventors: Moshiur M. Anwar, San Francisco, CA (US); Catherine Park, San Francisco, CA (US); Bernard Boser, Berkeley, CA (US)

(73) Assignee: Regents of the University of California, San Francisco, CA (US)

( * ) Notice: Subject to any disclaimer, the term of this patent is extended or adjusted under 35 U.S.C. 154(b) by 19 days.

(21) Appl. No.: 15/074,614

(22) Filed: Mar. 18, 2016

(65) Prior Publication Data
US 2016/0374559 A1   Dec. 29, 2016

(51) Int. Cl.
*A61B 1/07* (2006.01)
*A61B 5/00* (2006.01)
*A61K 49/00* (2006.01)

(52) U.S. Cl.
CPC .......... *A61B 5/0071* (2013.01); *A61B 5/0084* (2013.01); *A61K 49/0032* (2013.01); *A61K 49/0058* (2013.01); *A61K 49/0067* (2013.01)

(58) Field of Classification Search
None
See application file for complete search history.

(56) References Cited

U.S. PATENT DOCUMENTS

| | | | |
|---|---|---|---|
| 5,590,660 A * | 1/1997 | MacAulay | A61B 1/043 600/160 |
| 6,485,413 B1 | 11/2002 | Boppart et al. | |
| 8,574,859 B2 * | 11/2013 | Lin | A61B 5/0059 422/68.1 |
| 9,304,280 B2 * | 4/2016 | Gulari | G02B 7/027 |
| 9,314,304 B2 * | 4/2016 | Lee | A61B 18/24 |
| 2003/0138378 A1 * | 7/2003 | Hashimshony | A61B 5/0075 424/9.6 |
| 2006/0165350 A1 * | 7/2006 | Gelikonov | A61B 5/0066 385/33 |
| 2011/0009702 A1 * | 1/2011 | Morishita | A61B 1/00096 600/178 |
| 2011/0059016 A1 | 3/2011 | Ramanujam et al. | |
| 2012/0224053 A1 * | 9/2012 | Vykoukal | B01L 3/502715 348/135 |
| 2014/0303452 A1 * | 10/2014 | Ghaffari | A61B 1/05 600/301 |

* cited by examiner

*Primary Examiner* — Kennedy Schaetzle
(74) *Attorney, Agent, or Firm* — Davis, Brown, Koehn, Shors & Roberts, P.C.; Sean D. Solberg

(57) ABSTRACT

An imager for in vivo viewing of diseased tissue by way of fluorescently conjugated molecules. A generally planar imaging surface with a microlens array. The imager may be modular, such that a plurality of generally planar imaging surfaces can be used to image various aspects of disease tissue simultaneously. Certain implementations include an angle-selective imager, wherein light from substantially perpendicular to the plane of the imager is received, while incident light is selectively eliminated.

20 Claims, 24 Drawing Sheets

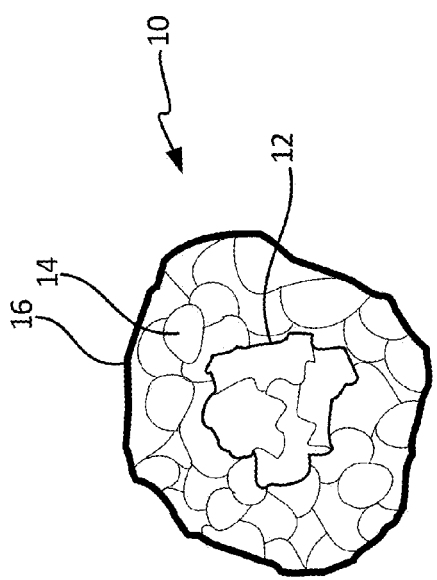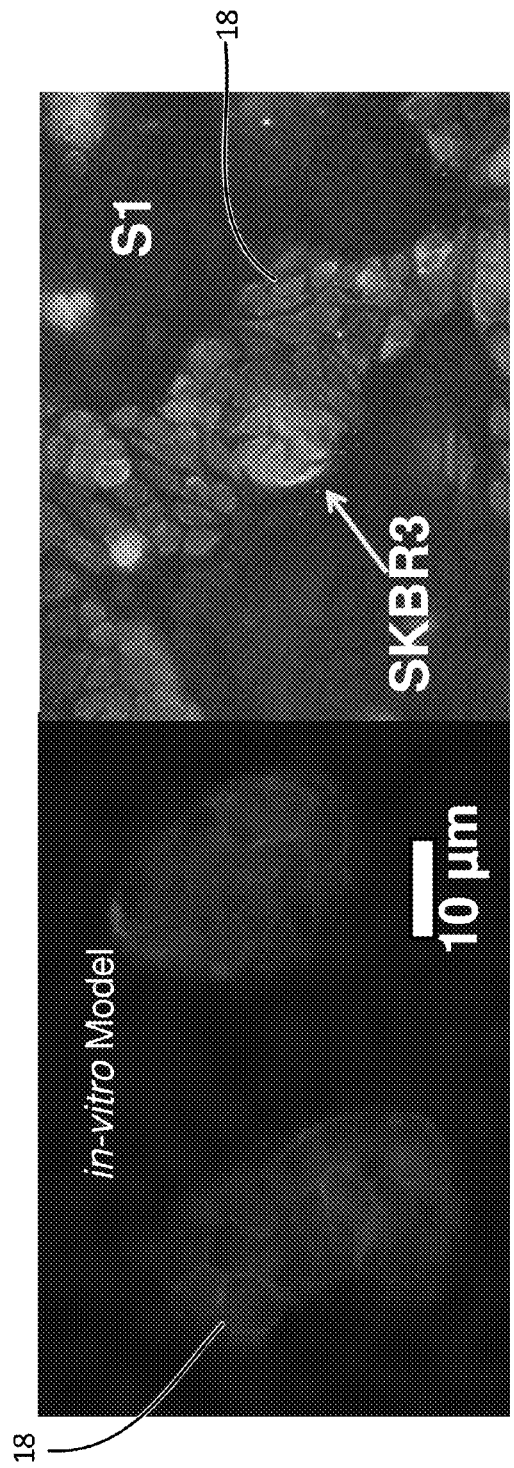
Fig. 1A
Fig. 1B
Fig. 1C

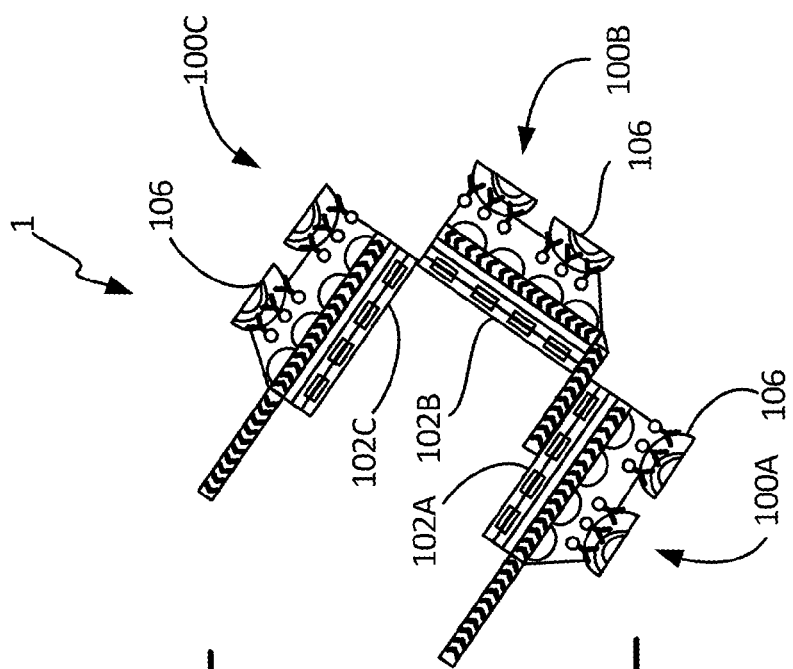
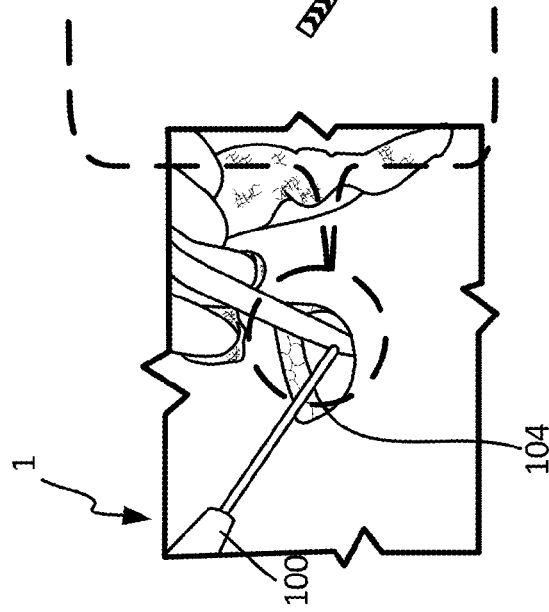
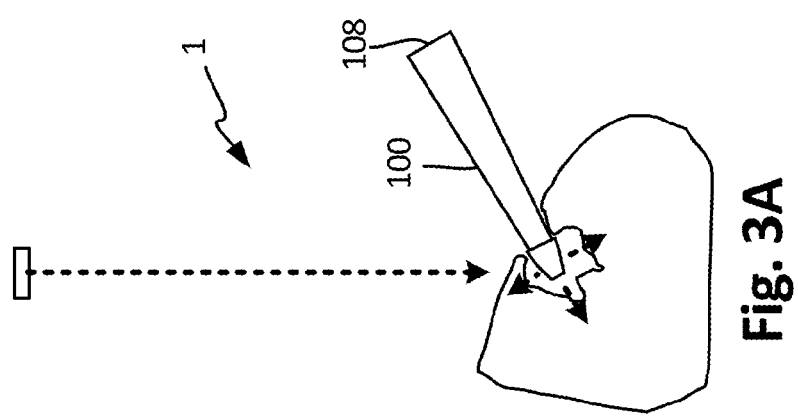

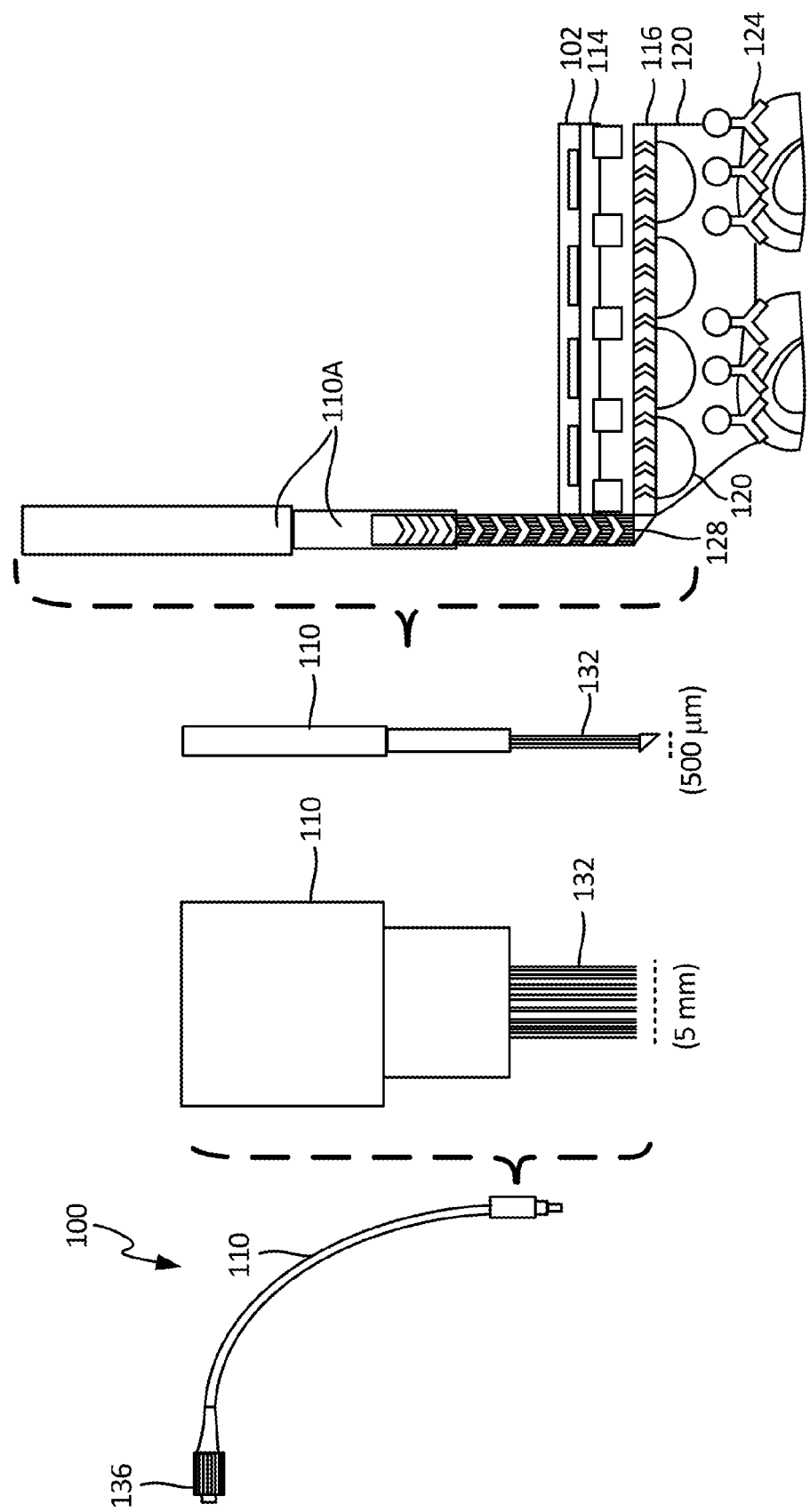

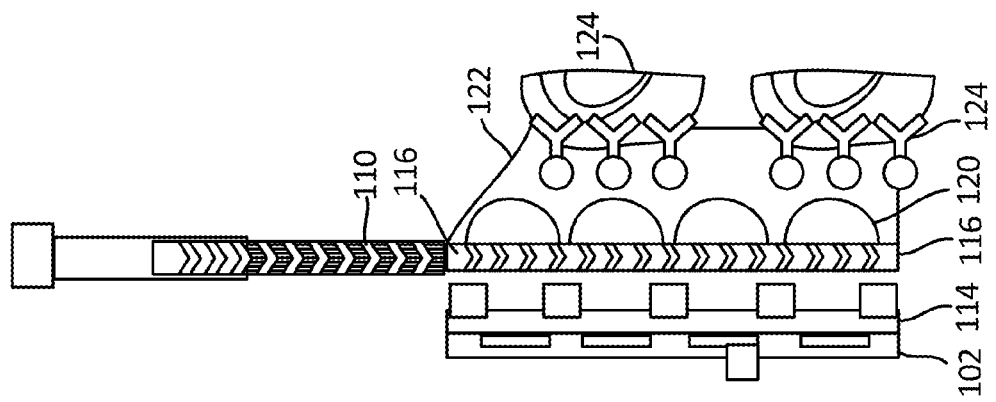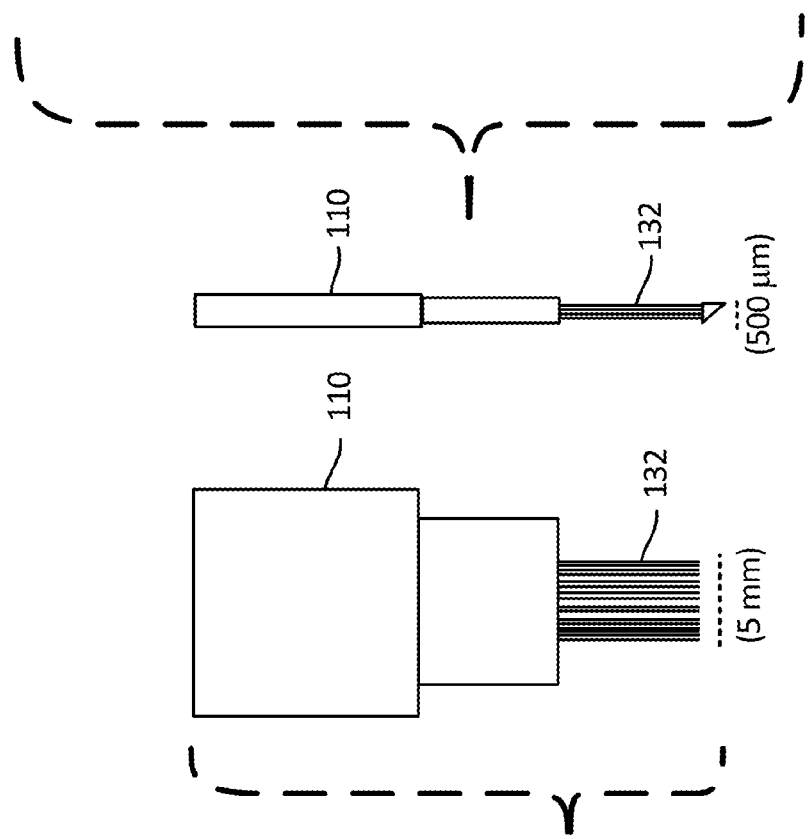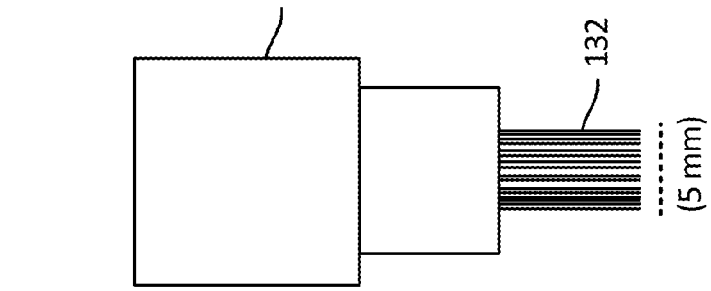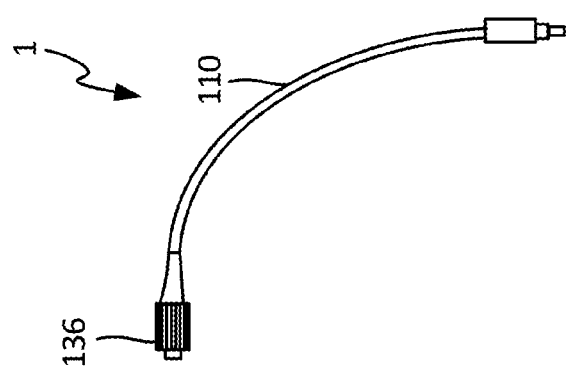

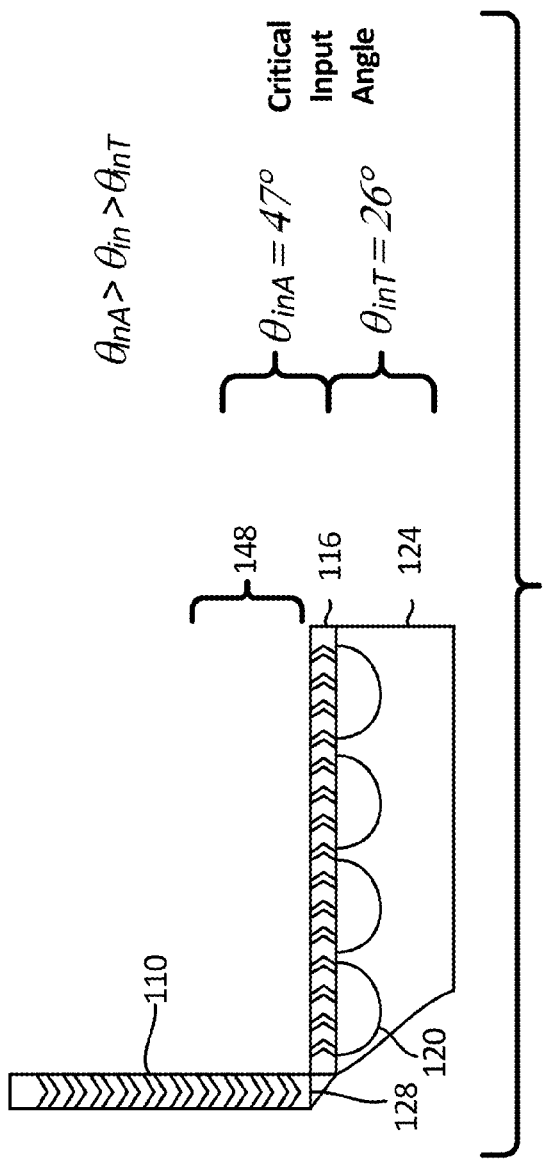
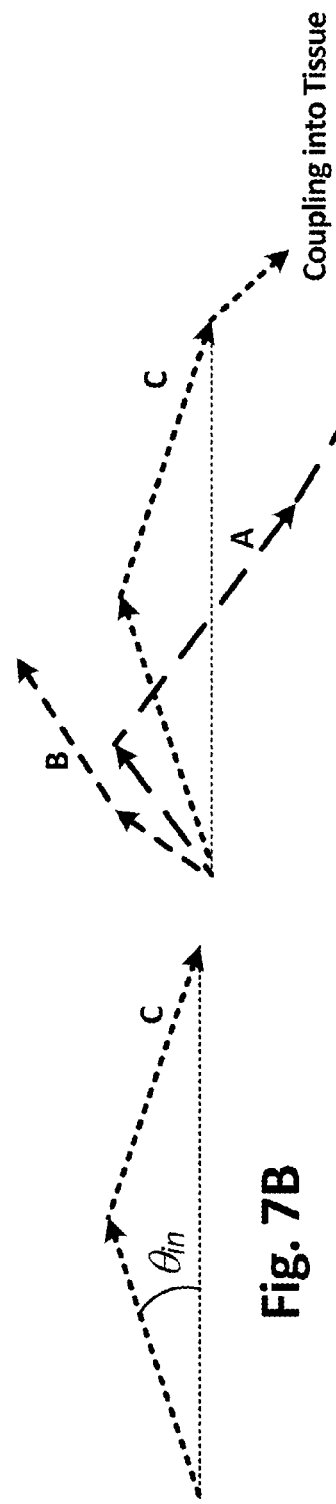
Fig. 7A
Fig. 7B
Fig. 7C

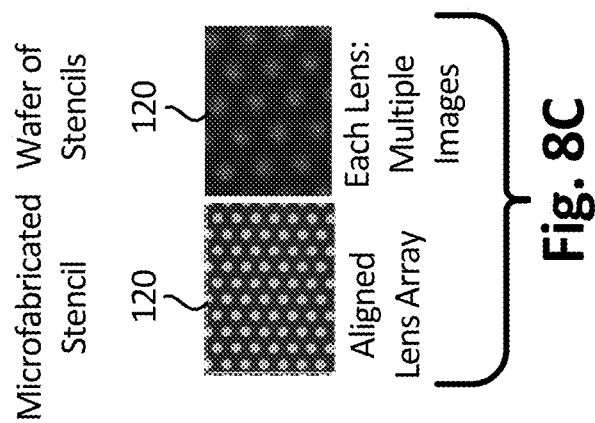
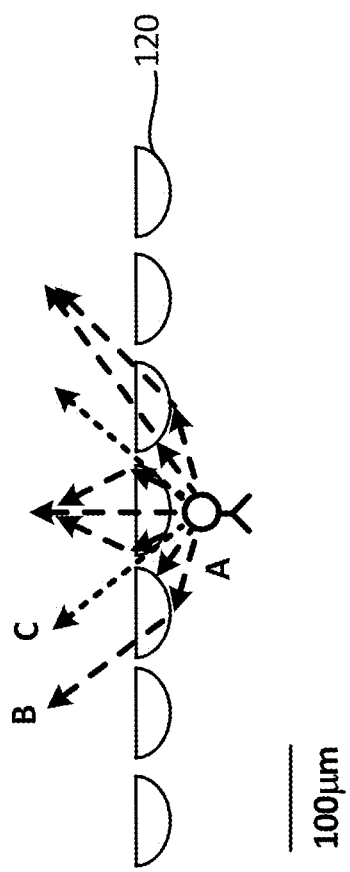
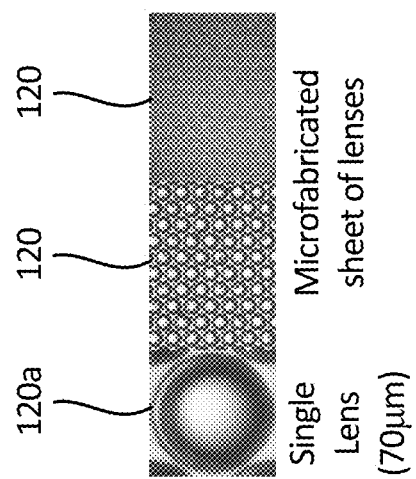
Fig. 8A
Fig. 8B
Fig. 8C

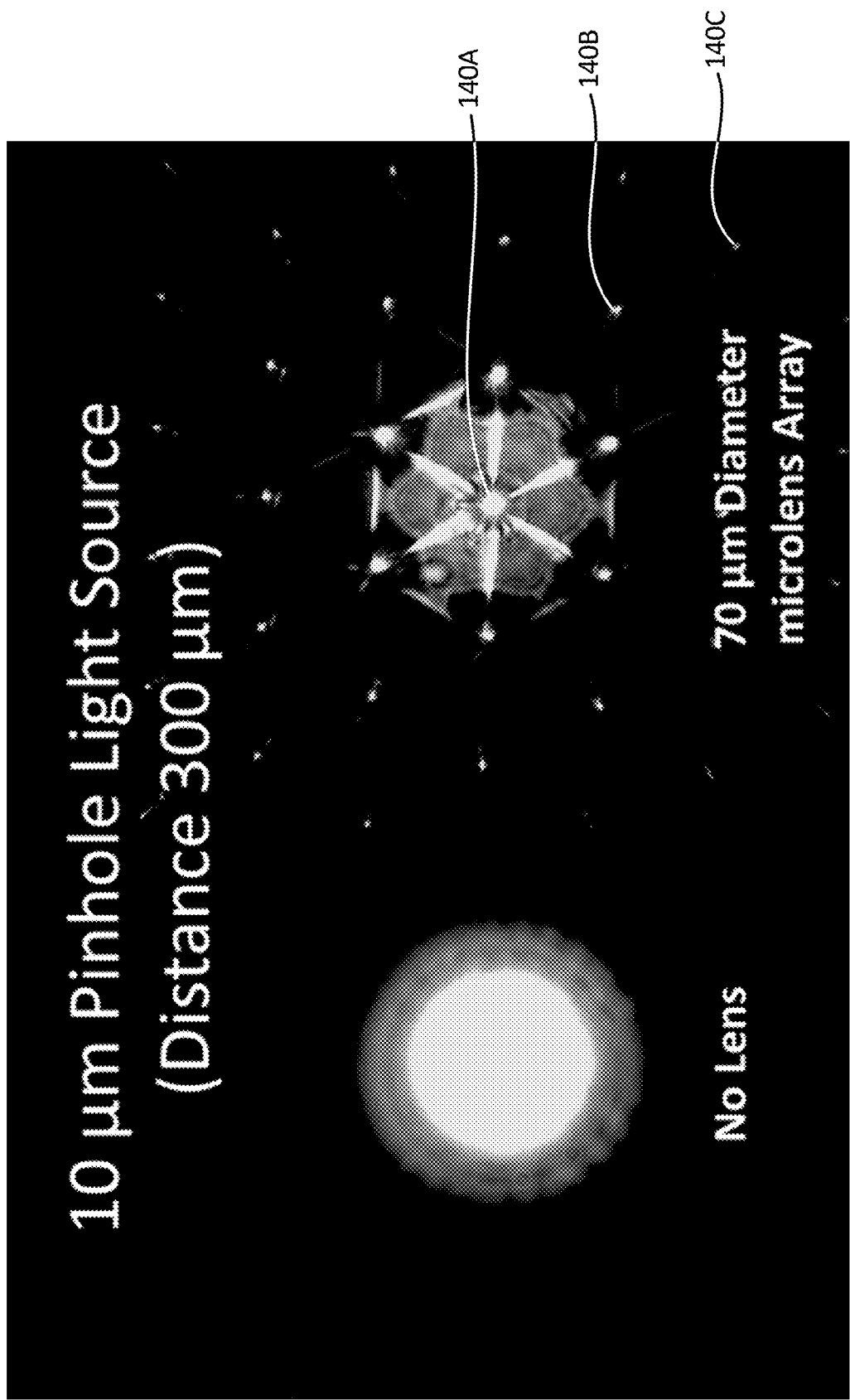

METHODS, SYSTEMS, AND DEVICES FOR IMAGING MICROSCOPIC TUMORS

FEDERALLY SPONSORED RESEARCH OR DEVELOPMENT

This invention was made with government support under grant no. TR000004 awarded by the National Institutes of Health. The government has certain rights in the invention.

CROSS REFERENCE TO RELATED APPLICATIONS

This application claims the benefit under 35 U.S.C. §371 to International PCT Patent Application No. PCT/US14/56788, filed on Sep. 22, 2014, which claims priority from U.S. Provisional Application 61/880,750, filed Sep. 20, 2013, and entitled "Methods, Systems, And Devices For Imaging Microscopic Tumors," both of which are hereby incorporated herein in their entireties by this reference.

TECHNICAL FIELD

The embodiments disclosed herein relate to an imaging device for visualizing microscopic disease in an intraoperative environment.

BACKGROUND

Successful treatment of early stage cancer, such as prostate and breast cancer, depends on completely resecting all disease, while sparing normal tissue. Consequently, the surgeon is faced with a difficult clinical decision: remove an additional margin of healthy appearing tissue, risking additional morbidity or risk leaving microscopic disease behind. Microscopic residual disease (MRD) leads to increased local recurrence (LR) and, potentially, reduced overall survival (OS). Therefore patients are often subjected to additional treatment (such as re-resection, radiation, and/or chemotherapy) to reduce the chance of recurrence; a result that could have been avoided if the entire tumor was initially removed. Although crude methods exist to evaluate tumor in the operating room, definitive identification of MRD can only be determined days later after molecular staining and microscopic visualization of the excised specimen in a pathology laboratory, rendering it ineffective for intraoperative guidance.

Identification of MRD is a prime concern in almost every oncological case. The device presented here is meant to be a platform imager for use with any disease subsite where surgical resection is necessary for cure, and for which there is a targeted agent capable of labeling and identifying the cancer cell. One example is breast cancer, whereby microscopic tumor is left in the tumor bed in one out of four operations. Microscopic residual disease doubles the rate of recurrence and thereby decreases overall survival. Therefore a repeat operation is essential. This could have avoided if all disease was resected during the initial operation. Another example is in prostate cancer, where a positive margin (another term for microscopic residual disease) increases the chance of cancer recurrence. Due to the morbidity of reoperation, patients with MRD are advised to receive postoperative radiotherapy, lasting approximately 6 weeks with significant cost and additional side effects. These are just a few examples of tumors types whereby leaving disease behind results in poorer oncologic outcomes or necessitates additional treatment. Therefore, there is a strong need to intraoperative identify MRD within the tumor bed to guide complete resection in a single surgery preventing both the morbidity and cost associated with multiple therapeutic procedures.

Although methods of intraoperative imaging for tumor tissue exist, these implementations are microscopes restricted to line-of-sight imaging far from the tumor bed due to their bulky size and rigid optics, preventing visualization of the majority of the tumor bed and resulting in poor sensitivity since the optical signal from the fluorophore deteriorates as the distance-squared. Fiber-optic approaches are not flexible enough to visualize small complex tumor cavities, and have too small a visual field to effectively visualize the entire tumor bed. Therefore, the device described in this patent solves these problems by employing a novel approach of placing the imaging sensor directly on the tumor bed surface, increasing sensitivity. To obtain cellular level resolution, combined with the ability to maneuver within the tumor bed, small fluorescent microscopes (on the order of a 100 microns) are patterned in a large array. This enables each microscope-element to visualize a population of roughly 100-200 cells, while the entire array operates in parallel, effectively imaging the entire tumor bed rapidly.

BRIEF SUMMARY

In Example 1 a system for imaging biological material in a patient, comprises a fluorescently conjugated molecule capable of binding to the biological material; a light source; a fiber optic light guide; an elongate probe sized for placement inside the cavity of the patient, further comprising at least one substantially planar detection surface, the detection surface further comprising an imager; a waveguide in luminary communication with the light source and an optical filter; and a visualization system in electrical communication with the probe, wherein the waveguide is capable of emitting light toward the biological material, such that the biological material's emitted fluorescence is received by the imager for display by way of the visualization system.

Example 2 relates to the system for imaging biological material in a patient according to Example 1, further comprising a microlens array.

Example 3 relates to the system for imaging biological material in a patient according to Example 1, wherein the imager further comprises at least one photodiode.

Example 4 relates to the system for imaging a biological material according to Example 3, further comprising a complementary metal oxide semiconductor process.

Example 5 relates to the system for imaging biological material in a patient according to Example 1, further comprising a charge-coupled device process.

Example 6 relates to the system for imaging biological material in a patient according to Example 2, further comprising a waveguide stencil configured to eliminate oblique light from reaching the microlens array.

Example 7 relates to the system for imaging biological material in a patient according to Example 1, wherein the fluorescently conjugated molecule binds biological material selected from the group consisting of: breast cancer cells, prostate cancer cells, cancer cells inside a tumor bed, cancer cells surrounding a tumor bed, disease cells in the microenvironment surrounding a tumor bed.

Example 8 relates to the system for imaging biological material in a patient according to Example 1, wherein optical filter is directly patterned on the imager surface.

Example 9 relates to the system for imaging biological material in a patient according to Example 1, wherein the waveguide further comprises a plurality of optical gratings.

Example 10 relates to the system for imaging biological material in a patient according to Example 1, further comprising a surgical tool, wherein the elongate probe is operationally coupled with the surgical tool.

In Example 11, an angle selective imager, comprises a light source further comprising a light guide; an elongate probe sized to be positioned within a body cavity of a patient undergoing surgery, wherein the device is operationally coupled with the light source by way of the light guide, said device further comprising at least one substantially planar detection surface, the detection surface further comprising; an imager further comprising a plurality of pixels and a microlens array; and a visualization system in electrical communication with the probe capable of computing and displaying fluorescence wherein the detection surface is adapted to allow light from substantially perpendicular angles from surface to pass through the microlens to the imager, and exclude light incident form other directions.

Example 12 relates to the angle selective imager according to Example 11, further comprising a micro-grating.

Example 13 relates to the angle selective imager according to Example 11, further comprising a nano-grating.

Example 14 relates to the angle selective imager according to Example 11, further comprising at least one cylinder disposed adjacent to the microlens array adjacent to an imager pixel.

Example 15 relates to the angle selective imager according to Example 14, further comprising a waveguide, wherein the waveguide is in luminary communication with the light guide.

Example 16 relates to the angle selective imager according to Example 15, further comprising an optical filter, wherein the waveguide is capable of emitting light toward fluorescently-tagged cells such that emitted fluorescence is passed through the microlens array and nano-grating and received by the imager.

Example 17, a modular system for imaging fluorescently tagged disease cells, comprises at least one imager further comprising a plurality of pixels; at least one waveguide further comprising at least one remote light source, wherein the at least one remote light source is capable of emitting light through the at least one waveguide to fluoresce the tagged cells; at least one microlens array configured to direct light to the imager pixels, wherein the at least one microlens array, imager and waveguide are disposed in a substantially parallel and planar fashion facing the tagged cells so as to transmit light substantially perpendicularly from the tagged cells to the imager by way of the microlens array.

Example 18 relates to the modular system for imaging fluorescently tagged disease cells according to Example 17, further comprising an optical filter.

Example 19 relates to the modular system for imaging fluorescently tagged disease cells according to Example 18, further comprising an additional modular system disposed to face an alternative plane of tagged disease cells.

Example 20 relates to the modular system for imaging fluorescently tagged disease cells according to Example 18, wherein the modular system further comprising an angle sensitivity grating. While multiple embodiments are disclosed, still other embodiments of the disclosure will become apparent to those skilled in the art from the following detailed description, which shows and describes illustrative embodiments of the disclosed devices systems and methods. As will be realized, the devices, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 1A depicts a cross-sectional overview of diseased tissue.

FIG. 1B depicts a field of cells fluoresced by way of a secondary label.

FIG. 1C depicts a field of cells fluoresced by way of a primary conjugated antibody.

FIG. 3A. depicts a schematic overview of certain exemplary embodiments of the imager as applied to a patient's body cavity.

FIG. 3B depicts one embodiment of the imager inserted into a body cavity of a patient.

FIG. 3C depicts a cross-section of the embodiment of FIG. 3B, showing the multiple imagers possible.

FIG. 5A is a side view of an exemplary embodiment of the light guide, according to one embodiment.

FIG. 5B depicts a front view of the light guide according to the embodiment of FIG. 5A.

FIG. 5C is a side view of the light guide, according to the embodiment of FIG. 5A.

FIG. 5D is a side view of the imaging system showing the light guide of FIG. 5A with a probe and imager observing tissue.

FIG. 6A is a front view of an exemplary embodiment of the light guide,

FIG. 6B depicts a side view of the embodiment of FIG. 6A.

FIG. 6C is a side view of the light guide, according to the embodiment of FIG. 6A.

FIG. 6D is a side view of the imaging system showing the light guide of FIG. 6A with a probe and imager observing tissue, wherein there is no reflector.

FIG. 7A depicts a side view of the waveguide and microlens array, according to an exemplary embodiment.

FIG. 7B depicts an angle of refraction, according to an exemplary embodiment.

FIG. 7C depicts various angles of refraction, according to certain embodiments.

FIG. 8A depicts various angles of light travel through the microlens array, according to one embodiment.

FIG. 8B depicts various bottom views of the lens, according to an exemplary embodiment.

FIG. 8C depicts various alternative views of the microlens and stencil, according to several embodiments.

FIG. 11A depicts light which has not been passed through a microlens.

FIG. 11B depicts light which as passed through a microlens array.

DETAILED DESCRIPTION

Figure 2:
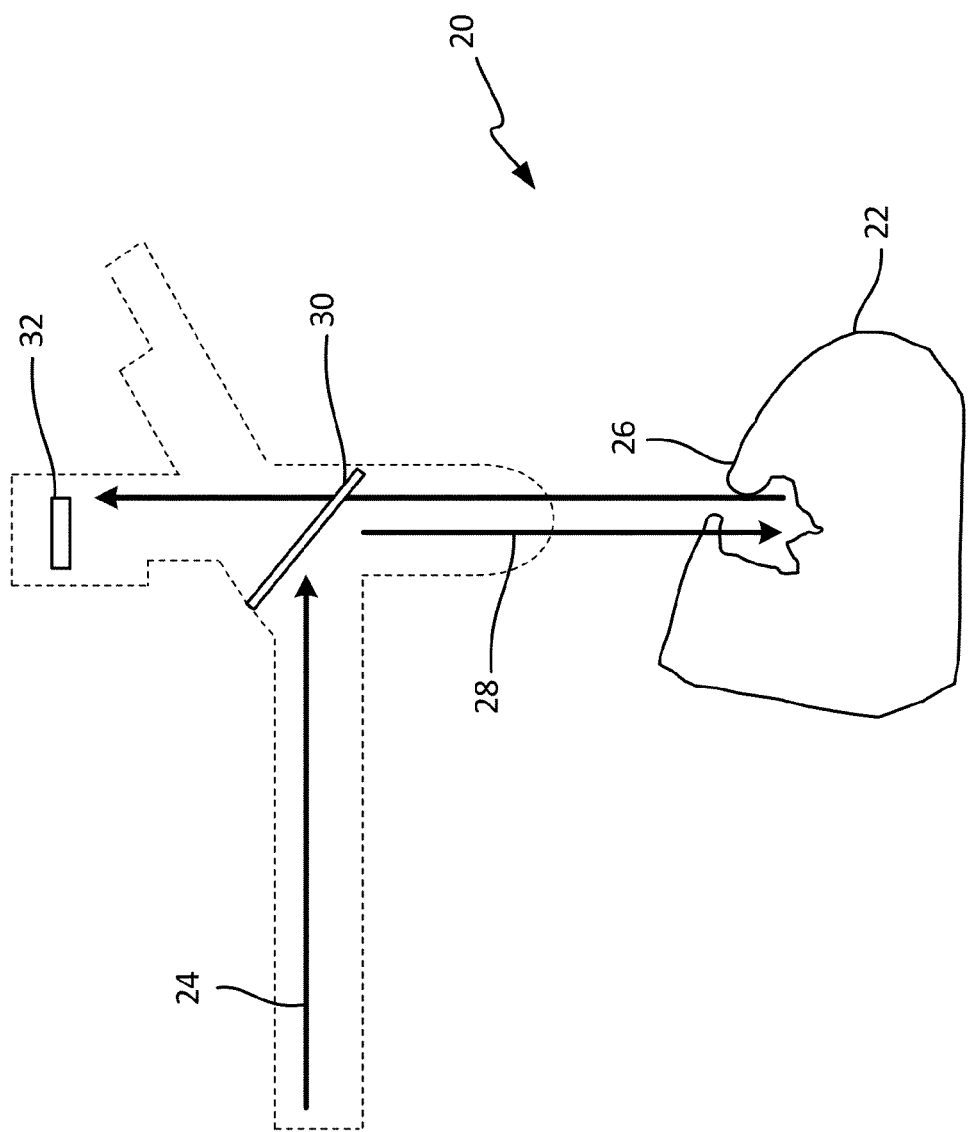
FIG. 2 depicts an overview of a prior art imager.

The various systems and devices disclosed herein relate to devices for use in medical procedures. More specifically, various embodiments relate to imaging devices, systems and methods for visualizing microscopic disease in an intra-operative environment. Certain exemplary implementations relate to imaging systems, devices, and methods for visualizing microscopic breast cancer. It is understood that the various embodiments of the system and related methods disclosed herein can be incorporated into or used with any other known medical devices, systems and methods.

The configuration of the system presents numerous advantages over the prior art. When performing a resection with current technologies, a surgeon is left with a difficult decision: first, to remove more normal tissue, which can result in poor functional and cosmetic outcomes, such as has historically been done with mastectomy in the case of breast can cancer (and currently in the developing world), or second, to excise only the suspected tumor (for example with lumpectomy in breast cancer), but risk a greater chance of cancer returning because the practitioner missed removing microscopic disease. As examples, in breast cancer 1 in 4 women has disease left behind, doubling the local recurrence rate in these women, and leading to a decrease in overall survival. Therefore another operation to re-exise the tissue is required. Similarly in prostate cancer, in up 10-50% of men, tissue can be left behind, but due to the morbidity of re-excision in the prostate bed, these patients must be treated with post-operative radiation, adding significant cost and toxicity to the treatment. As is shown in FIG. 1A, the tissue area 10 comprises a cancerous (gross disease) area 12 surrounded by normal tissue 14, which may contain some microscopic traces of disease tissue, and an edge 16, wherein the tissue ceases to contain any traces of disease tissue. This makes identifying and resecting microscopic disease vital. There is significant difficulty in identifying cancerous cells during the removal of a tumor, because isolated foci of tumor cells cannot be seen with current intraoperative imaging tools or felt.

The configuration of the system presented here offers numerous advantages over the prior art enabling visualization of microscopic disease. The approach presented here utilizes a fluorescently-tagged molecule that is pre-operatively injected and binds to the tumor within the patient's body. FIGS. 1B-1C depict the comparative ease of in vitro identification when using labeling. In FIG. 1B, SKBR3 (HER2 overexpressing breast cancer cells) were grown on a bed of Si (normal) cells, and labeled with primary anti-Her2 and a secondary antibody (In FIGS. 1B-1C, labeled cells signified with reference number 18). In FIG. 1C, SKBR3 cells are identified using an anti-Her2 antibody conjugated to Alexa 647. Any fluorophore can be used, although those in the near-infrared range have better tissue penetration and are therefore preferable. By way of example, LICOR's IRDye 800CW dye and indocyan green, for example, can be used. Further embodiments include conjugation of the molecularly targeted agent (such as anti-Her2 antibody) to fluorophores. In various embodiments of the system, primary and/or secondary fluorescent antibodies targeting any number of disease tissues may be used with quantum dots. The quantum dots are fluorescent nano-particles that do not bleach, and can be illuminated at any wavelength less than 700 nm, and still emit at 700 nm, making them extremely robust fluorophores. As quantum dots are not yet FDA approved, and to avoid the need for secondary labeling in an in vivo/clinical setting, in the present Example Alexa 647 was conjugated directly to an anti-Her2 antibody, as would be apparent to one of skill in the art. The single anti-Her2 antibody labeling 22 is depicted in FIG. 1C. While this example of the implementation of the system is illustrated in breast cancer, use of the system can be extended to any other cancer where complete surgical excision is necessary for cure (such as prostate cancer).

The systems and devices disclosed herein are configured to be used in combination with labeling of target diseased cells similar to that described in FIGS. 1B-C. Further, in exemplary embodiments, a wide array of fluorescent conjugates can be utilized. While Indocyanine green is the only fluorescent dye with current FDA approval, a wide array of dyes may be utilized. In certain embodiments, any fluorescent conjugate with an excitation frequency of about 640-800 nm and an emission frequency of about 660-820 nm may be utilized, as would be apparent to one of skill in the art. Exemplary embodiments of the system use specifically targeted and tagged FDA-approved antibodies to label targeted cells in vivo and visualize them with a novel imaging device. In certain embodiments, these antibodies may be conjugated to a fluorophore, though other antibody conjugates are possible, as would be apparent to one of skill in the art. The use of such fluorescent antibodies and other molecular labeling techniques allow the use of the various embodiments of the novel imaging device (or "probe" or "imaging probe") to detect the presence of these labeled tumor cells for visualization and resection. In certain embodiments, a modular approach is adopted, such that the provided imagers can be assembled in a variety of shapes, sizes, and configurations depending on the specific application. Accordingly, certain implementations feature a three-dimensional imaging configuration. In further implementations, the imager may be directly integrated into another surgical instrument. Exemplary embodiments also feature a planar form factor, as is described herein.

Initial diagnosis of breast cancer often begins with physical exam and/or mammogram. Currently, to confirm the diagnosis of breast cancer, a biopsy is then taken and molecular subtyping is done. For example, a biopsy may confirm the presence of ductal carcinoma in situ ("DCIS") or invasive cancer, and staining or genetic (such as mRNA) analysis can be done to determine Her2 overexpression. Mueller-Holzner E, Fink V, Frede T Marth C. *Immunohistochemical determination of her2 expression in breast cancer from core biopsy specimens: a reliable predictor of her2 status of the whole tumor*. Breast Cancer Research and Treatment 2001; 69:13-19; Pusztai L, Ayers M, Stec J, et al. *Gene Expression Profiles Obtained from Fine-Needle Aspirations of Breast Cancer Reliably Identify Routine Prognostic Markers and Reveal Large-Scale Molecular Differences between Estrogen-negative and Estrogen-positive Tumors*. Clinical Cancer Research 2003; 9:2406-2415; Ross J S, Fletcher J A, Bloom K, J., et al. *Her-2/neu Testing in Breast Cancer*. Am J CLin Pathol 2003; 120:S53-S71. As with other cancers, the tumor itself consists of an area of gross disease surrounded by an invisible area of microscopic disease.

The various embodiments and examples described herein relate to enabling the visualization of fluorescent or luminescent molecules within the body as well as on tissue excised from the body. The disclosed embodiments are applicable to any disease which presents a selective biological (or inorganic) agent capable of identifying the diseased cell. The description disclosed herein focuses on cancer as an exemplary application, but those of skill in the art will readily identify other possible applications. The various disclosed embodiments are thus capable of illuminating cells located within the body (or excised tissue sample), and gathering, focusing and optically filtering (to remove background light) the fluorescently emitted light. Collectively, and for brevity, the disclosed apparatus, systems and methods will be referred to herein as "the imaging system," which comprises an "imaging probe" comprised of an imager and a probe in operational communication with an external monitor. However, the use of any of these terms is in no way intended to limit the scope of the described embodiments to a specific modality.

Thus, in exemplary embodiments, the imaging system comprises an imaging probe configured to be inserted into the body cavity of a patient and capable of transmitting a signal to an external monitor. In certain embodiments, the imaging probe is configured to be integrated with another medical device, such as a scalpel or within another device, such as a DaVinci system.

In such embodiments, light is generated from an external source and guided to the imager which captures, converts, and transmits this signal into an image relayed to the user by way of an operational connection. In certain embodiments, various aspects of the probe and imager can be fabricated in a planar format, in any size, as will be apparent from the present disclosure. In certain embodiments, to be easily placed within the body, the diameter of the probe and sensor should be less than 2-3 cm. This planar structure can potentially be bent to create a 3D structure, or multiple planar devices can be put together to create a 3D structure, enabling simultaneous imaging in multiple directions to more efficiently image a complex surface or cavity. Accordingly, by way of the probe, the imager can be brought near to, or in contact with, tissue, and can be integrated within another surgical instrument as desired.

Although not all cancers have a distinctive cell surface marker amenable to antibody labeling, many common cancers do, including prostate cancer (Taneja S S. *ProstaScint (R) Scan: Contemporary Use in Clinical Practice*. Rev Urol 2004; 6 Suppl 10:S19-28) head and neck squamous cell carcinoma (Cetuximab Blick S K A Scott L J. *Cetuximab: a review of its use in squamous cell carcinoma of the head and neck and metastatic colorectal cancer*. Drugs 2007; 67:2585-2607) and Her2 overexpressing breast cancer (Hortobagyi G N. *Trastuzumab in the Treatment of Breast Cancer*. New England Journal of Medicine 2005; 353:1734-1736). Various other examples are possible. In the presently presented embodiment, the system is demonstrated with a Her2 overexpressing breast tumor, which comprises approximately ⅕th to ⅓rd of all breast cancers and in which the effect of MRD on recurrence and survival is well studied. In the US alone, this cancer results in roughly 60,000 Her2+ lumpectomies annually.

In the various embodiments contemplated herein, if the patient is Her2+, the patient's cancerous cells can be labeled prior to surgery. That is if the patient is Her2+, under certain embodiments of the system the surgeon can then preoperatively inject the patient with fluorescently labeled Herceptin (an antibody that specifically targets Her2) approximately 24-72 hours before the surgery. In such embodiments, the antibody specifically binds to (and thus labels) the Her2+ tumor cells within a patient's body, including both the gross and microscopic aspects of the disease. This strategy has been demonstrated in multiple animal studies, as well as a current clinical trial in the Netherlands.

In various embodiments, other common cancer subtypes can also be labeled. For example, many breast cancers are estrogen receptor (ER) and/or progesterone receptor (PR) positive, and a fluorescently labeled estrogen or progesterone molecule (or antibody against the receptor) can be used to label these cells in vivo. Furthermore, many cancers, including breast cancer, are "PET-Avid," meaning that they have high glucose uptake due to their elevated metabolic activity. In these embodiments, commercially available fluorescently labeled glucose molecules can be injected pre-operatively in the same manner as a fluorescently-labeled antibody to specifically target and label the cancerous cells, as would be apparent to one of skill in the art. Furthermore, there are cancer specific targeted molecules, such as those developed by Blaze Biosciences ("Tumor Paint"), and Avelas Biosciences (AVB-620).

Previously, despite the ability to identify the tumor using in vivo molecular labels, no known imaging device existed capable of allowing the acute visualization of the MRD cells, thus leaving gross resection as the only option for clinicians.

In use according to certain embodiments of the system, after the initial resection the surgeon is able to utilize the imager to scan and identify any residual tumor(s) in the tumor bed with the custom-imaging probe, ensuring complete resection in a single operation. In exemplary embodiments the surgeon is capable of visualizing cancerous cells in vivo, during the procedure, by utilizing a microfabricated imager directly within the tumor bed, thus imaging the resection bed microns from the surface and obtaining a thorough high resolution scan of the entire tumor bed.

As shown in FIG. 2, prior art imagers typically utilize a single large microscope 20 placed above a patient 22, wherein excitation light 24 is transmitted into the tumor bed 26 and sensed by an external lens 28, filter 30, and imager 32. This approach has two principle disadvantages. First, the rigid optics of a microscope limit the view to line of sight only. Because the tumor bed is a small, complex cavity, this approach misses the vast majority of the tumor bed surface, especially the side portions. Second, because of the size of the microscope and lens, cells must be imaged from outside the tumor bed. This substantial working distance decreases resolution, making it difficult, if not impossible to both identify a focus of 200 cells on the tumor bed surface and thoroughly and rapidly image the entire surface area of about 5 cm$^2$. In another embodiment, the probe is directly integrated with the resection tool (for example a scalpel or bovie), and cellular imaging information is processed in real time by way of the visualization system (described below).

One embodiment of the imaging system comprises an imaging probe with a microscopic fluorescent imager at the tip, capable of being placed and manipulated within the tumor cavity while imaging foci of microscopic residual foci of cancer cells after initial surgical excision. The patient's pathologic cells are labeled prior to surgery by systemically injecting a biologic, conjugated to a fluorescent molecule specifically targeted against specific disease cells. By way of example, in certain embodiments Herceptin for HER2 over-expressing breast cancers may be used. Other examples include, but are not limited to, Prostacint for prostate cancer; Cetuximab for head and neck and colorectal cancer; or glucose conjugated to a fluorescent molecule for imaging hyper-metabolic (typically cancerous) cells.

In these embodiments, the imaging system consists of an array (or arrays) of imagers each simultaneously fluorescently imaging a small area of the tumor bed. Since the optical signal is diminished by the square of the distance covered, placing the imager near or against the tumor bed allows the user to obtain an exponentially greater signal. In certain exemplary embodiments, and in order to illuminate the tumor bed lying underneath the opaque imager, the imagining system utilizes a novel approach wherein the light around and along the sensor surface, using an optical waveguide to illuminate the tumor bed. The labeled cancer cells will fluoresce, and we gather and focus the light by using an array of microlenses. A microfabricated optical interference filter removes background light, and an imager then resolves the image produced by each microlens, translating it to a signal alerting the surgeon to an area of cancer cells. The imager can be an angle selective imager, which in addition to recording the spatial intensity of light, preferentially images specific angles of incoming light, helping to eliminate cross-talk between the adjacent micolenses.

FIGS. 3A-C and 4 depict a schematic overview of certain exemplary embodiments of the system 1. In these embodiments, an imaging probe 100 comprises an imager 102 which is configured to be placed inside a cavity 104 left by a resected tumor to identify labeled disease cells 106. In these and other embodiments, the imaging probe 100 can be attached at the distal end of a handle or other operational tool 108. In certain embodiments, the imaging probe 100 transmits the detected results out of the body of the patient, as described in detail below. As depicted in FIG. 3C, in certain embodiments, the imaging probe 100 has a plurality of sides 100A, 100B, 100C, each comprising an imager 102A, 102B, 102C, thus allowing the collection of imaging data from numerous aspects. Thus, by way of example, in certain embodiments a surgeon is able to scan the tumor bed and be visually alerted to individual diseased regions. This can be accomplished by either the operator visualizing the image directly form the sensor, or an image that has been processed using computation techniques to highlight the area of cancer cells. The resulting image can, for example, also be viewed as a reconstruction on a laptop or other monitor (as described in relation to FIG. 24). Still further, in certain embodiments the imaging system can be configured to alert the surgeon when a threshold level of signal is detected, as would be apparent to one of skill in the art.

Figure 4:
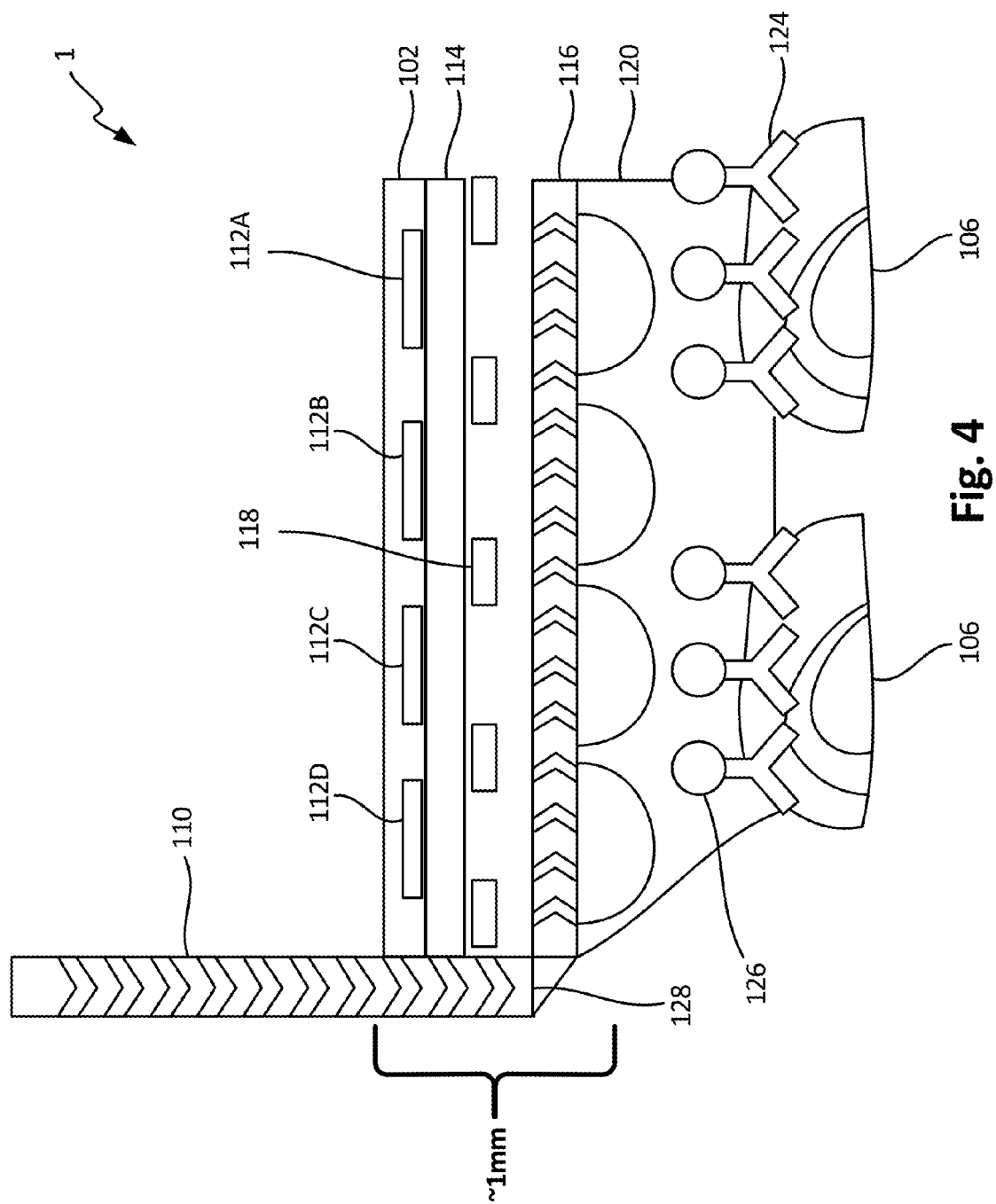
FIG. 4 depicts a detailed schematic overview of the imaging system, according to an exemplary embodiment.

Exemplary embodiments of the imaging system minimize the distance between the probe 100, imager 102 and the tumor bed surface 124. FIG. 4 depicts a detailed overview of an exemplary arrangement of the system showing the operational structure of the imager 102. In these exemplary embodiments, the probe has a remote light source (not shown) that provides illumination light via a light guide 110, the imager 102 further comprising a plurality of individual pixels 112A, 112B, 112C, 112D, an optical filter 114, a waveguide 116, a waveguide stencil 118 and a microlens array 120. In exemplary embodiments, these components are understood to be disposed in a generally planar fashion to the extent that is possible, and layered adjacent to one another as provided, so as to create a generally planar imaging surface 122. Transmission and processing of the resulting images is discussed herein in relation to FIG. 25 In certain experimental embodiments, the system features "macro-scale" components, such as a glass slide wave guide, or an off the shelf filter), without lenses. The total thickness of the imager 102 in this exemplary implementation is 1.5 cm. As would be apparent to one of skill in the art, other sizes are of course possible.

In certain implementations, a tumor bed 124 in which the cells are labeled with specific fluorescent-tagged antibodies 126 is observed. In various embodiments, the imager 102 may be a sensor, a photo-detector or other device capable of transducing a light signal into an electrical signal, as would be known in the art. As is apparent in FIG. 4, the imager 102 is located within the cavity and adjacent the tumor bed. In certain implementations, a reflector 128 is employed to alter the direction of light transmitted by way of the light guide 110. Current imaging methods, as noted above, use a lens above the tumor bed to gather and focus light. Because light diverges over a distance, this results in a significant loss of signal. Therefore, the closer the light can be projected by the imager to the tumor bed surface as in the embodiments herein, the more light can be gathered by the imaging probe. One of the challenges presented by placing the imager inside the cavity is the illumination of the cavity such that the fluorescence may be detected. In the exemplary embodiments of the system described herein, the proximity of the light source and imager to the tumor bed results in the necessary illumination. Because the system utilizes an imager placed within the tumor bed, rather than above it, and because the imager is opaque, exemplary embodiments of the system employ various apparatuses designed to guide the light around the imager surface, thus illuminating the tumor bed.

In certain exemplary embodiments, and as a means of visualizing in a wider field of view, at least one imager may be mounted parallel to the fiber optic light guide such that the fiber optic light guide and waveguide are substantially in axis, rather than at an angle. For example, in FIGS. 6A-D, the plane of the light source (designated by reference arrow A) and waveform (designated by the reference arrow B) are in substantially the same orientation (as opposed to incorporating the reflection shown in FIGS. 5A-C).

As is shown in FIGS. 5A-D, certain exemplary embodiments of the system are capable of guiding light along the imaging surface 122 by way of a light guide 110 in order to illuminate the tumor bed while the imaging surface 122 is placed directly on the tumor bed surface 124. To accomplish this and introduce versatility, exemplary embodiments use a remote light source which emits light through the light guide 110, through the waveguide 116, such that the light source can be positioned far from the operative field (not shown). These implementations allow the use of any wavelength or power, and do not place any size or shape restraints on the source, thus allowing for flexibility and cost savings.

Numerous light sources can be used. In various embodiments, the light source can consist of a laser, laser diode, light emitting diode ("LED"), or halogen or mercury arc lamp. Other sources are possible, as would be apparent to one of skill in the art. In one exemplary embodiment, the system utilizes a remote LED light source, which presents the advantages of being quickly turned on and off and having relatively high power. Other sources have various advantages that can be utilized to suit individual needs. Another advantage of having the LED remote or separate from the patient is that significant heat can be generated by the LED and LED power supply.

In these embodiments, an optical filter can be placed in front of the remote LED light source to ensure that the wavelength of light is emitted in a narrow optical range (not shown). The LED directly couples to a fiber optic cable which is attached to the imaging probe (not shown). In certain embodiments, a commercially available LED that directly couples to a fiber optic cable is used (available, for example, from Thor Labs). The light is then guided into the tumor bed 124 by the waveguide 116.

Returning to the figures, FIGS. 5A-C depict an exemplary implementation of the probe 100 comprising a light guide 110. FIG. 5A depicts an overview of the imaging probe 100 and light guide 110. FIGS. 5B-C show front and side views, respectively, with FIG. 5D depicting a zoom schematic of one implementation of the light guide to diseased tissue 124. The waveguide 116 can consist of a planar structure as shown. Furthermore, an optical grating can be fabricated on the surface of the wavefacing the tumor bed 124 to facilitate the escape of light towards the tumor bed. This grating may consist of microfabricated ridges or a roughing of the surface. The grating density may be increased at the distal end of the waveguide to compensate for the decreased intensity of light at the distal end by allowing more light to escape, maintaining a uniform illumination along the surface.

As is shown, in certain embodiments a light guide 110 is provided which is generally elongate and comprises a light transmitting core 132. In exemplary implementations, this can be a fiber optic core, though other materials may be used. Certain embodiments further comprise a reflector 128 which is configured to alter the course of light transmitted by way of the light guide so as to illuminate the desired disease tissue. In order to simultaneously capture information from several angles, or in certain embodiments to capture a 180 degree view of diseased tissue 124, certain implementations of the probe 100 further comprise a 3 dimensional arrangement of sensors (like that shown in FIG. 3C). In these embodiments, in order to illuminate the side-facing imagers 102A, 102C, a similar fiber optic arrangement of a bundled fiber that terminates in a linear array of fibers can be used, without the 90 degree reflection (as is shown, for example, in FIG. 6D). In certain embodiments, the light can then be reflected 90 degrees as shown in FIGS. 4 and 5A, though in other embodiments various other degrees of reflection can be utilized. That is, the angle of the light as it is directed into the waveguide can range from 0 to 180 degrees. In certain embodiments, the reflector 128 can be a prism or a mirrored reflective surface. In certain embodiments, the fiber optic bundle guides light into the tumor bed and then terminates in a linear array of smaller fibers, each about 500 µm in diameter, with a microfabricated mirror to bend the light 90 degrees along the surface of the sensor. Other configurations of size and angle are of course possible. For example, in certain embodiments, best shown in FIG. 6D, a linear array (not bending 90 degrees) is used. This approach is useful for the "sides" of the imaging probe.

In exemplary embodiments, such as those of FIGS. 5A-C and 6A-D, the system comprises a multi-fiber core. In these embodiments, the multi-fiber core comprises 12 fibers packed together, and coupled to an LED (not shown). Other numbers of fibers and remote light sources are of course possible. In these embodiments, the light from the remote light source is guided down each of the individual fibers of the fiber optic core to the terminal end, wherein the individual fibers are aligned to form a linear array. To bend the light at the terminal end (90 degrees, for example, as depicted in FIG. 5C) the ends of the fibers are cut to a specified bevel (which is 45 degrees in the depicted example) and in certain embodiments can be coated with a mirrored surface, such as a microfabricated mirror. In certain embodiments, the optical fiber can be custom manufactured for this application by, for example, Doric Lenses. As shown in FIG. 5A, exemplary embodiments of the system also comprise a transmission cable 136 designed to convey the image signal received by the imager out of the probe and to a remote visualization or processing device (not shown).

In these embodiments, after the light has reached the terminal end of the light guide 110, the light is then transmitted down a waveguide 116, such as the waveguide implementations depicted in FIG. 4. In certain embodiments, the waveguide 116 may comprise a transparent material that has a higher index of refraction than air, and similar to the material in the fiber optic cable. By way of example, the higher refraction material can be similar to glass. Certain characteristic materials have minimal autofluorescence and minimal absorption in the optical region. Quartz is one such material, though others are possible. As will be described in further detail below with respect to FIG. 7, the waveguide allows the light being directed into the waveguide from the light guide to pass through the bottom portion of the waveguide (the portion closest to the tumor bed) toward the tumor bed, while helping to prevent light from being directed upward toward the imager.

In certain embodiments, the light transmitting core 132 and the optical waveguide 116 are coupled together with an optical epoxy. This optical epoxy can be utilized to bond the terminal end of the fiber optic cable(s) to the edge of the waveguide. In these embodiments, the optical epoxy should have an index of refraction similar to the waveguide and fiber optic cable(s). In certain embodiments, the waveguide further comprises at least one insulated wrapping 110A.

After being directed to the tumor bed 124 via the waveguide 116, the light induces fluorescence or other visual signals from the labels that are attached to the diseased cells, which is then passed back through the waveguide to the imager. In certain exemplary embodiments, the system comprises an optical filter, as shown in FIG. 4. In some of these embodiments, the optical filter is an optical interference filter, which allows only a desired signal (such as a particular fluorescent wavelength of light) to pass through to the imager 102. In these embodiments, the optical filter prevents background light, for example from the environment and the excitation light, so as to only allow the imager 102 to be reached by visual signals from the diseased cells. In certain exemplary embodiments, the ratio of the transmitted light to the blocked light can be around 104:1, and in certain embodiments the filter is about 500 µm thick, though other ratios and thicknesses can be used in the system, as would be apparent to one of skill in the art FIGS. 7A-C depict another principle aspect of the system, which is efficiently directing the filtered light from the waveguide 116 to the tumor bed surface 124 and concentrating it there by preventing it from escaping by way of an "air trap" created by differing indices of refraction. By way of example, FIG. 7A depicts the travel of the light down the waveguide 116 and illumination of the tumor bed 124. In these embodiments, the system utilizes the tissue of the body to direct, or "leak" light from the waveguide to the tumor bed and prevent, or "trap" it from directing upward toward the imager.

In practice, light will travel down the waveguide and be "trapped" inside the waveguide by the total internal reflection, as described further herein. Opposite the tumor bed from the waveguide (defined as the space between the imager and the waveguide) the system utilizes material with the lowest possible index of refraction, such that it is transparent, for example air 148. This is frequently known as an "air gap," though other materials, such as low-refraction polymers are possible. For example, if the index of the air gap is n=1, the waveguide is comprised of quartz (n=1.48), and the tissue/fluid of the tumor bed has an index of n=1.33, the light is preferentially trapped in the tissue/fluid and waveguide by this differential in index.

This air (or other lower-refraction material) "gap" serves to "trap" the light in the waveguide and prevents the light from "escaping" upward toward the imager 102. On the opposite (tumor bed-facing) side, the index of refraction of the tissue, saline, and/or blood will more closely match the index of refraction of the waveguide, allowing light to escape. FIG. 7C illustrates this phenomenon. Light is directed into the waveguide at $\Theta_{in}$, where $\Theta_{in}$ is sufficiently large to couple into tissue (line A in FIG. 7C), sufficiently small enough not to pass directly to the imager (line B in FIG. 7C). If $\Theta_{in}$ is too small, then it will not couple into the tissue (line C in FIG. 7B). By way of example, an exemplary calculation is shown for an air gap, quartz waveguide, and saline/tissue interface. In still another embodiment, a microfabricated grating or roughing of the surface is provided to allow light to escape the waveguide on that side. In exemplary implementations, a higher barrier created by the interface between the differing indices of refraction is preferable, though not required. In alternate embodiments, the optical waveguide can comprise high index material as another means of increasing the differentiation in index of refraction, although the optimum is an index of refraction closest to that of tissue and/or blood.

To achieve angles depicted in FIG. 7B multiple approaches are possible. In certain embodiments, fibers are angled with respect to the waveguide, for example fibers maybe perpendicular or angled at 30 degrees with respect to the waveguide. The angle can be adjusted by having a mirror that is a different angle than 45 degrees.

Figure 9:
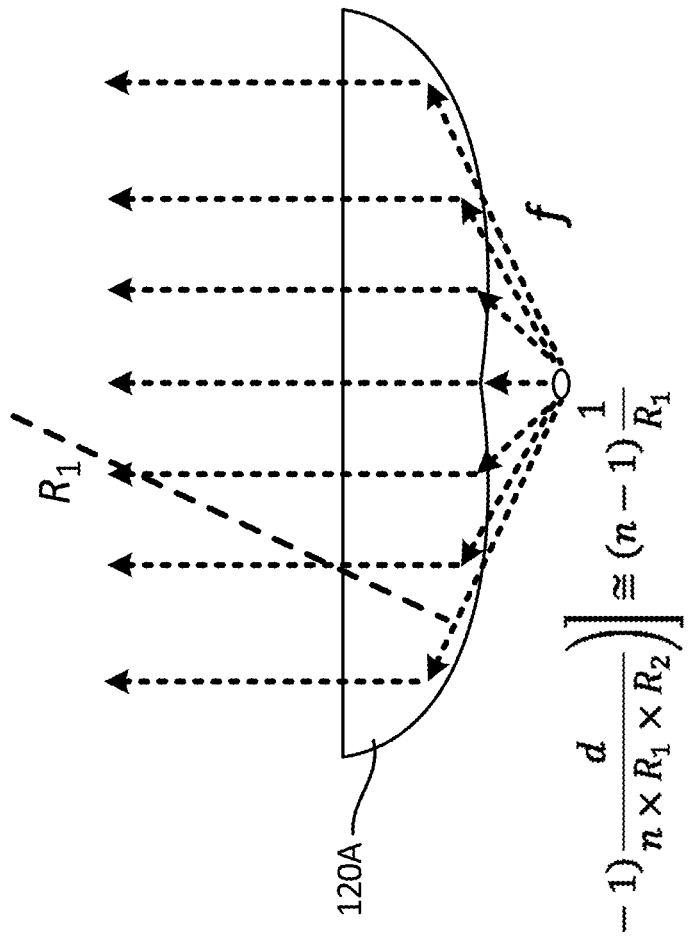
FIG. 9 depicts various routes of travel for light through a large lens.

FIG. 8A shows an overview of another exemplary embodiment of the system 1 relating to the use of the microlens array 120 and imager to collect and process the visual signal produced on the tumor bed. In this embodiment, the microlens array 120 redirects the light A, B, C cast on the imager at the individual lenses. Exemplary embodiments of the system utilize a three dimensional array of microfabricated fluorescent sensors to enable 180 degree imaging (best shown in FIG. 3C) from the close proximity of the imaging probe. As is shown in FIGS. 8B-8C, in exemplary embodiments, these microfabricated lenses 120 and stencils 118 can be fabricated in large sheets or on a substrate such as a quartz and assembled in "wafers" 150. In order to focus light at a very small distance from the sensor surface (for example 100-300 µm), extremely small lenses are utilized. Each "microlens" 120A will focus the light below it directly onto a pixel above, creating an array of thousands of fluorescent microscopes that can simultaneously image the tumor bed below. In one embodiment, as shown in FIG. 9, a plano-convex lens is used. In order to focus an object that is extremely close to a lens 120A, the Lensmaker's equation requires that the radius of the lens is:

$$R \cong f \times \left(\frac{n_1}{n_2} - 1\right) \quad (1)$$

where f is the focal length (in this case, distance to the tumor cell), and $$\frac{n_1}{n_2}$$

is the ration of indices of refraction of the lens ($n_1$=1.5) to the sample (e.g. tissue $n_2$=1.37), thus making R f×0.11 for this example. Therefore, to have a focal length "f" of a few hundred microns (to account for any fluid and tissue between the tumor cells and the sensor surface, the radius of the lens must be roughly ⅒th f. The radius is depicted as R1 in the figure. The radius of curvature of the planar side (R2) is set to infinite to approximate a flat surface. "d" is the thickness of the lens. To image the entire surface, these lenses are fabricated in a periodic array. In the example shown, they are arranged in a hexagonally packed array, with a diameter of roughly 70 microns. Therefore, instead of one large lens, the system utilizes an array of microlenses. In this exemplary embodiment, the microlens arrays have a radius of about 35 um, although microlens arrays of various other sizes can also be utilized in other embodiments.

As discussed above, FIG. 8A depicts an array of microlenses. This periodic array of microlenses results in an array of image recordings by the imager from individual foci. The microlens array creates a unique image: instead of a single image, a periodic array is generated (with each point in the array of light hitting the sensor at a different angle). However, in certain circumstances, the use of individual microlenses can create noise and/or blurring issues, as discussed further below.

As shown in FIGS. 10-25, the system utilizes a variety of approaches to ensure that the visual signal is clear and can be properly received and processed to yield accurate visualization. As such, various embodiments of the system also utilize a variety of means to address and reduce noise and blurring. In order to increase resolution and sensitivity, certain embodiments utilize an angle selective imager (discussed herein and below).

Figure 10A:
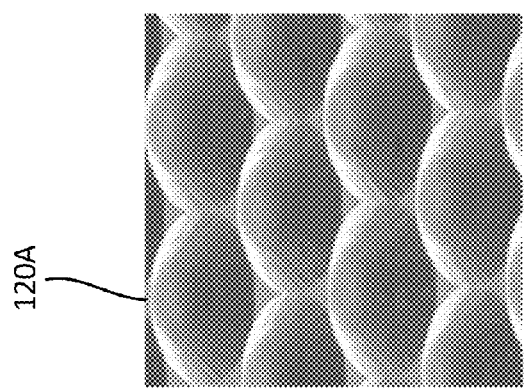
FIG. 10A depicts a perspective view of a microlens array, according to an exemplary embodiment.
Figure 10B:
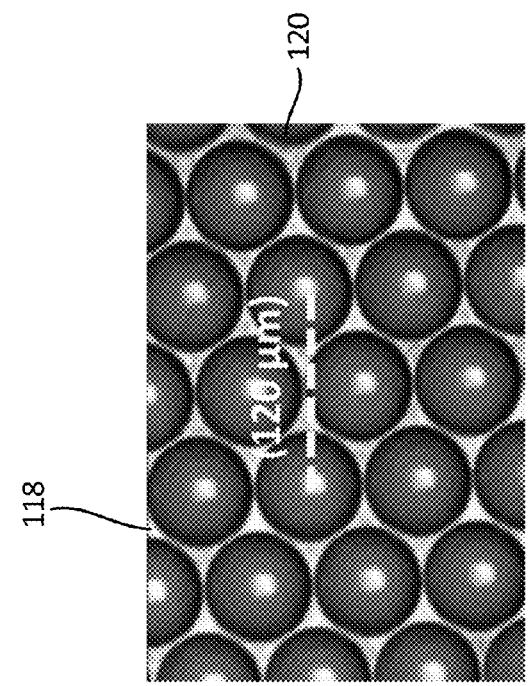
FIG. 10B depicts a scaled perpendicular view of the microlens array, according to an exemplary embodiment.

For example, and as shown in FIGS. 10A-B, in certain embodiments, the waveguide 116 further comprises a stencil pattern 118 matched to the microlens array 120, such that the light may pass through the lens 120 and the stencil pattern, which also serves to block any light that passes in between the lenses which is unfocused. These stencil patterns may be fabricated using photolithography, and an example wafer is also shown in FIG. 10B. Another embodiment of a lens array 120 may use a completely packed array whereby every point on the surface has a lens, such no light passes through unfocused.

Figure 10C:
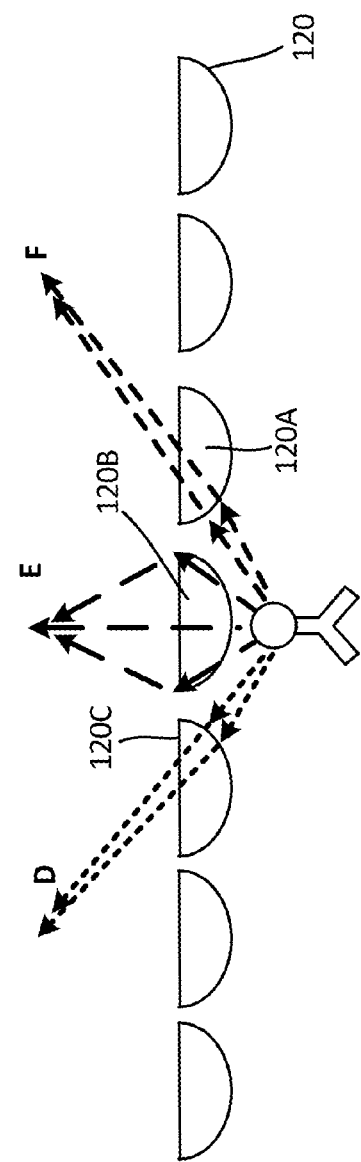
FIG. 10C depicts various routes of travel for light through the microlens array, according to an exemplary embodiment.

In embodiments utilizing a stencil pattern and waveguide, these components are aligned with the lens array. As shown in FIG. 10C, the microlens array 120 produces a periodic image due to the closely spaced lenses 120A, 120B, 120C with each lens forming a copy of the image at a different angle (designated by the light having reference letters D, E and F). This effect can be observed when looking at a point source of light 140, as is shown in FIGS. 11A-B, which shows an example 10 μm pinhole light source from a distance of 300 μm, both through no lens (FIG. 11A) and through a 70 μm diameter microlens (FIG. 11B), wherein the light 140A, 140B, 140C is received by a number of pixels owning to the multiple lenses in the array. As is apparent from FIGS. 11A-B, light passed through the pinhole without a lens is diffuse 140A, while light passed through the pinhole and lens is refracted 140B.

Figures 12A, 12B:
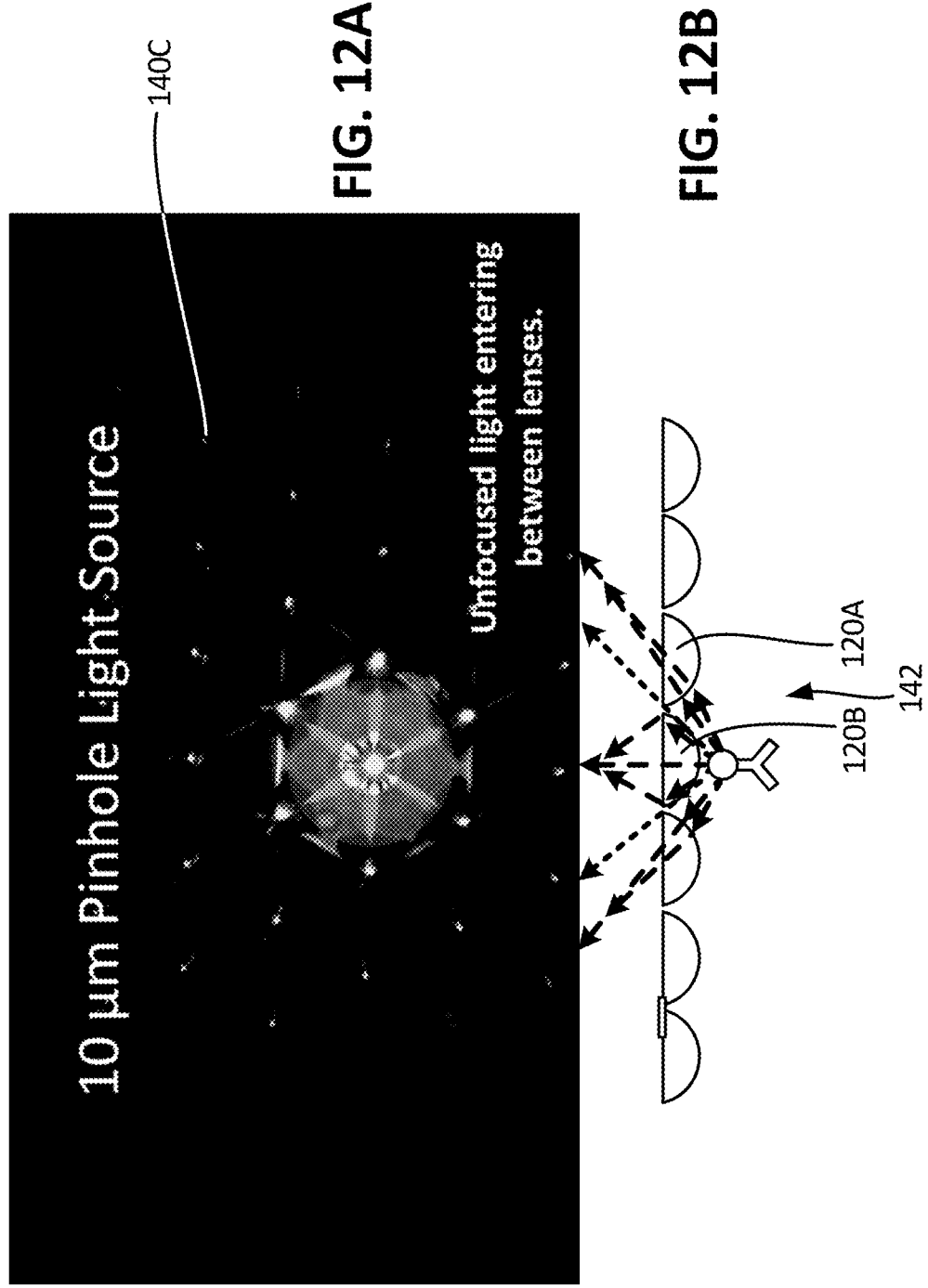
FIG. 12A depicts light passing through a 70 µm pinhole light source.
FIG. 12B depicts a cross-sectional sideview of light passing through a microlens array.
Figure 13A:
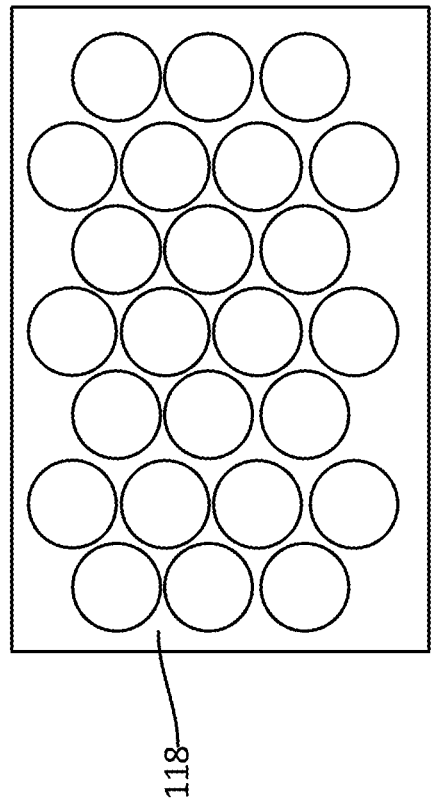
FIG. 13A depicts a top view schematic diagram of the waveguide with the stencil, according to an exemplary embodiment.
Figure 13B:
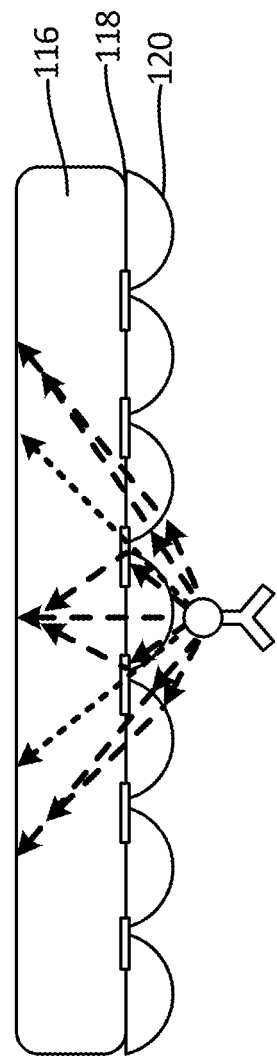
FIG. 13B depicts a sideview of the stencil adjacent to the microlens array.

In exemplary embodiments, the space between the lenses allows light 140 to pass unfocused. Therefore, the area between the lenses must be blocked, or the lenses need to be arranged so as to be flush or adjacent to one another, as is shown in FIGS. 12A-B. In FIGS. 12A-B, unfocused light 140D is shown escaping through the gaps 142 between the lenses 120A, 120B, thus causing unfocused light to reach the imager (as represented by the light at 140C in FIG. 12A). In certain exemplary embodiments of the system, the opaque waveguide stencil 118 (shown in FIGS. 13A-B) is used to prevent the passage of light between gaps in the microarray (as shown in FIG. 13B).

Additional aspects of the imaging system address the control over the focal distance. Cells that are at a distance not equal to the focal length will appear blurred, but each image will still be confined to the spatial area subtended by a single microlens. Accordingly, regardless of the focal distance, the poorest resolution is equal to the diameter of the microlens. In the best circumstance, where the tumor bed is directly in focus, the focus will depend on the quality of the lens, approaching 1-10 μm. By way of example, a 70 μm resolution is adequate for the purposes of imaging microscopic residual disease.

Figure 14A:
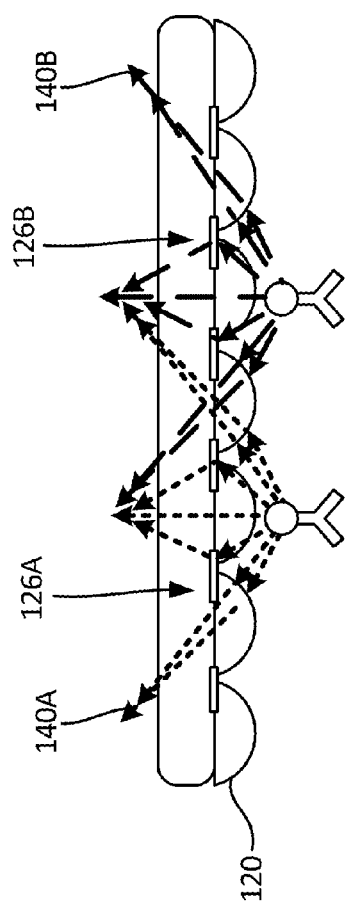
FIG. 14A depicts a sideview of a microlens array with a stencil disposed opposite two antibodies, according to an exemplary embodiment.
Figure 14B:
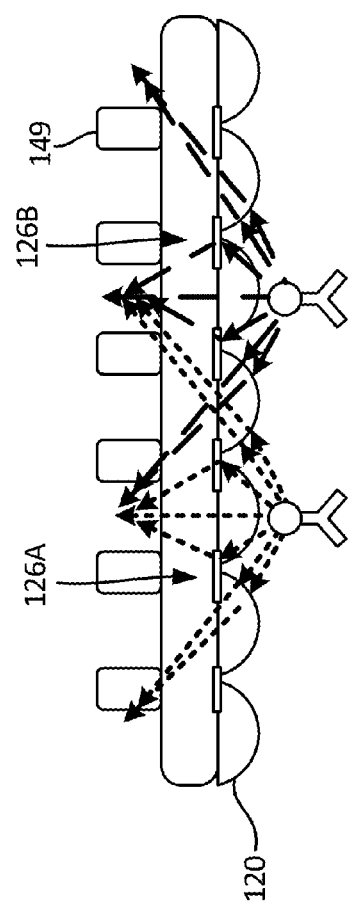
FIG. 14B depicts a sideview of a microlens array with a stencil disposed opposite two antibodies further comprising a angle selective imager, according to an exemplary embodiment.
Figure 14C:
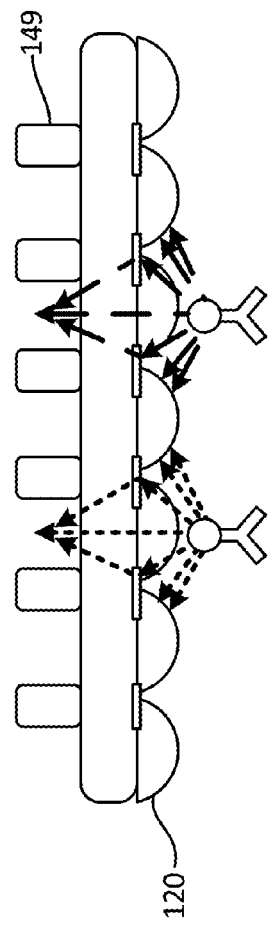
FIG. 14C depicts a sideview of a microlens array with a stencil disposed opposite two antibodies further comprising a angle selective imager, according to an exemplary embodiment, with light being selected.

Micro arrays may also present a cross-talk and blurring problem, which is addressed in exemplary embodiments of the system. As shown in FIGS. 14A-C, because each lens array 120 produces multiple images, there can be cross talk from neighboring lenses, making the image blurry (in FIGS. 14A-B, designated by the light 140A, 140B emitting from the neighboring labeled antibodies 126A, 126B). Certain exemplary embodiments of the system utilize a high resolution imager as a means of addressing cross-talk. In exemplary embodiments, this high resolution imager can be coupled with a processor so as to deconvolve and/or back-calculate to reduce any angular noise. This requires a high degree of focus. Another means utilized by certain embodiments is to isolate the signal by physically isolating the received signal to that which is directly opposite the individual microlens.

Figure 15:
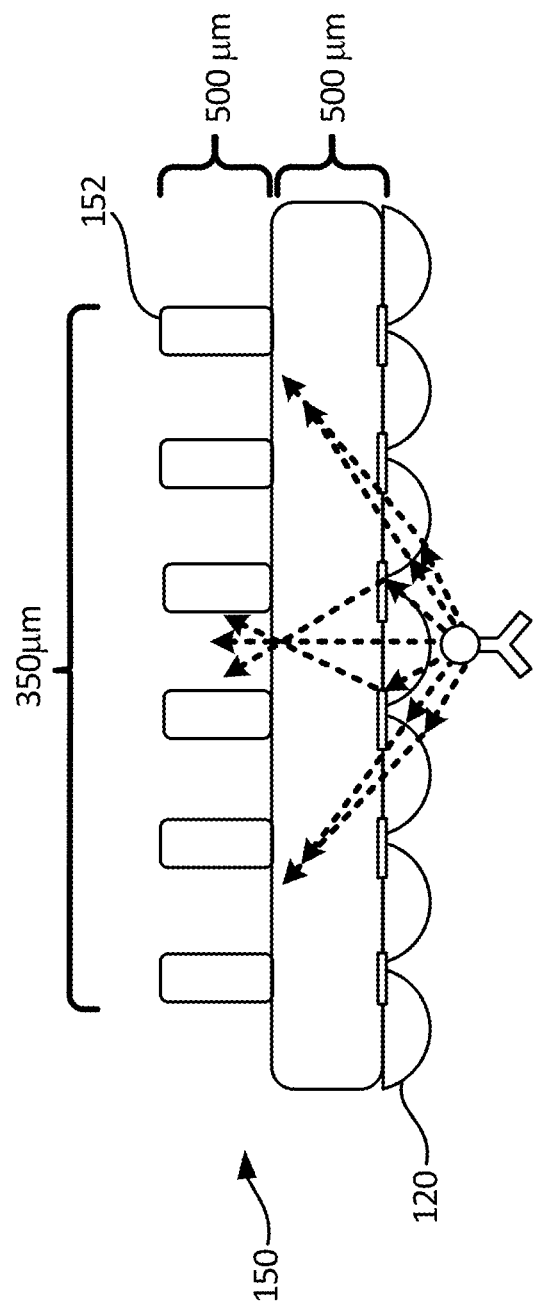
FIG. 15 depicts a sideview of an embodiment of the imaging system comprising micro-gratings.

Therefore, to image only the lens directly below and eliminate any light that is reaching the imager at an angle other than perpendicular, certain exemplary embodiments also utilize an angle selective imager 149, as shown in FIGS. 14B-C, which prevents cross-talk (as is shown in FIG. 14C). There are several strategies that can enable angle sensitivity in the system. The first is to use a micron scale grating on certain embodiments of the system, as shown in FIG. 15. This micro-grating only allows certain substantially perpendicular angles from the tumor bed to the imager to pass through to the imager. These micro-gratings thus impose a threshold pattern on the acceptance of light through the lens by physically limiting the angles of light which may enter. In certain embodiments, this grating can be the pitch of the lens array, for example 500 μm tall, and can be made from a silicon wafer or other similar material. In certain embodiments, the these can be collimators of varying dimensions. For purposes of the following examples, the "nano" being 1-10 μm in diameter, and the alternatives being in the range of 10 to several hundred microns.

Figure 16B:
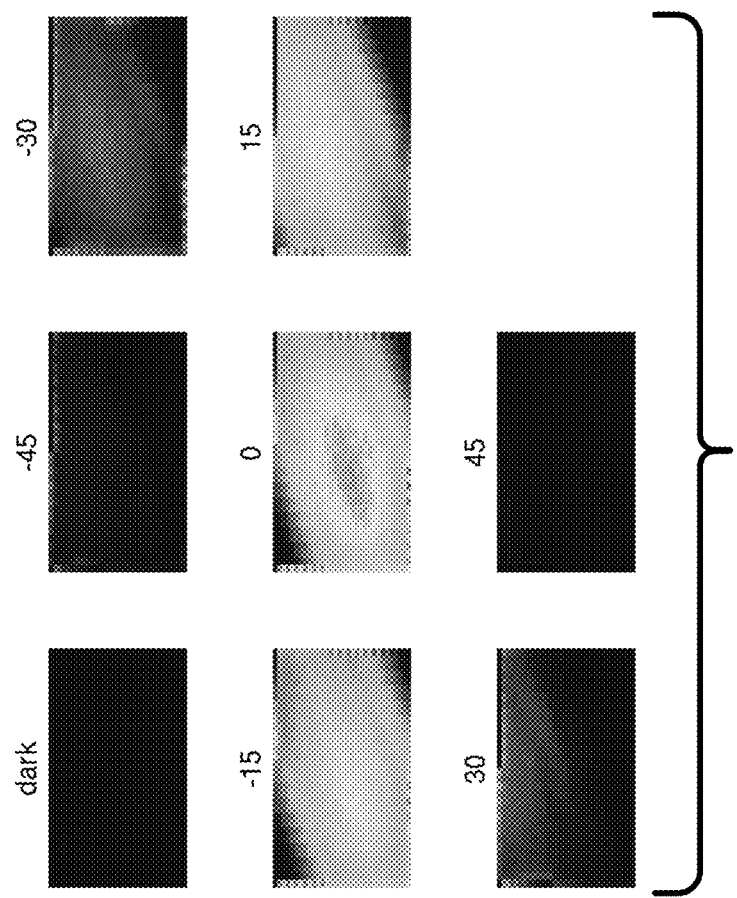
FIG. 16B shows a variety of images taken at varying incident angles.
Figure 16A:
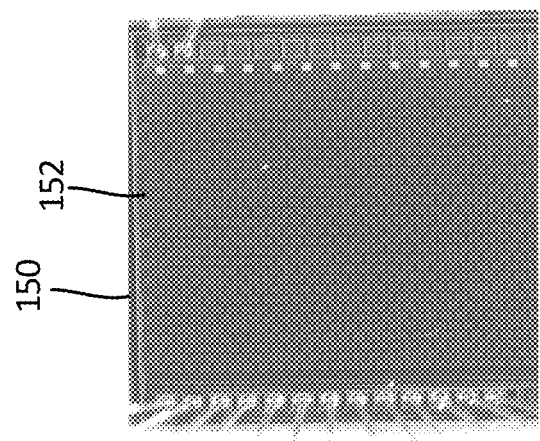
FIG. 16A depicts an embodiment of the imaging system comprising an angle-selective nano-grating.

FIG. 16A depicts an alternative approach to system angle selectivity: an angle selective imager with nano-grating. By utilizing wiring available on an integrated circuit imager, the system can further comprise a grating 150 further comprising small "cylinders" 152 disposed adjacent to the array (not shown). In embodiments utilizing this approach, the grating 150 is microfabricated directly on the imager itself (not shown). FIG. 15 depicts one embodiment of an angle selective imager using a complementary metal oxide semiconductor process (CMOS). In further embodiments, smaller scale geometric arrangements can be constructed. In embodiments utilizing this technique, the thickness of the "micro"-grating was reduced or eliminated, allowing the sensor to be placed closer to the surface of the tumor bed, thereby improving the signal. The aperture of the nano-grids should be greater than the wavelength of light used to avoid diffraction. The spacing of the grids is also determined by the fabrication process. In the embodiment shown, a CMOS process is used, and the metal interconnects are used to fabricate the gratings. In still further embodiments, other processes, such as a low-dark current photodiode, charge-coupled device (CCD), or PIN diodes can be used. In certain embodiments, the device is fabricated to have one pixel under each microlens. Greater pixel densities are possible and the greater the pixel density the higher the resolution. For purposes of illustration, cylinders 2.4 microns wide and 8 microns tall have been used in certain embodiments, though other sizes and shapes are possible. In these embodiments of the system, the cylinders only allow light that is substantially perpendicular to the surface to pass through. In the experiment, a custom microfabricated 2.5 mm×2.5 mm angle selective imager having 180 nm features and 1024 pixels was utilized (FIG. 16A). In this embodiment, each pixel corresponded to the size of a microlens. Other configurations are of course possible, as would be apparent to one of skill in the art. Using this approach, the image was taken from a variety of angles (ranging from +/−45 degrees) and the results were recorded (FIG. 16B). As would be apparent to one of skill in the art, various sizes and arrangements can be utilized. As is apparent from this study, the grating successfully prevents incident light from passing to the pixels.

After light passes through the lens array, wavelengths of light different form the fluorescent or luminescent emission wavelength of the molecular label are eliminated by an optical filter. In the present embodiment the filter is a multi-layer interference filter patterned on a 500 um glass wafer substrate. In certain embodiments, the filter is epoxied onto the imager. The filter may also consist of material that blocks light at wavelengths different from the emission wavelength of the molecular label. In other embodiments the optical filter is patterned directly on the image sensor.

Figure 17C:
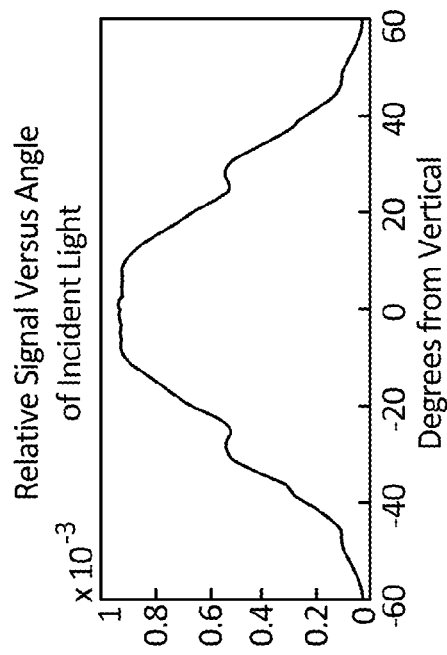
FIG. 17C depicts the simulation of gratings at various angles, according to certain embodiments.
Figure 17A:
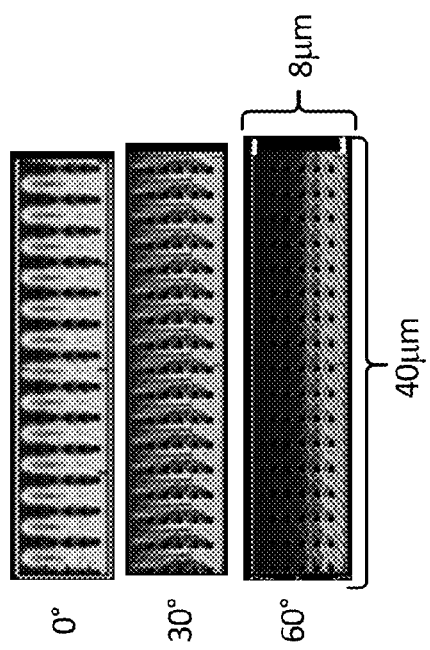
FIG. 17A depicts a schematic of the nano-gratings receiving emitted light of a variety of angles, according to an exemplary embodiment.
Figure 17D:
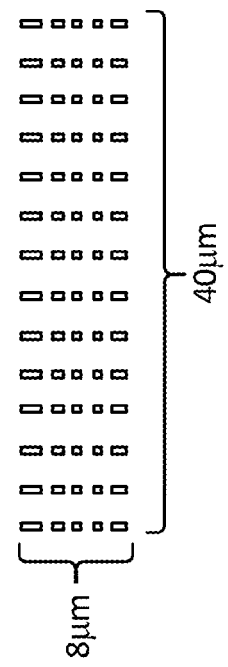
FIG. 17D depicts the relative signal compared to the angle of incident light.
Figure 17B:
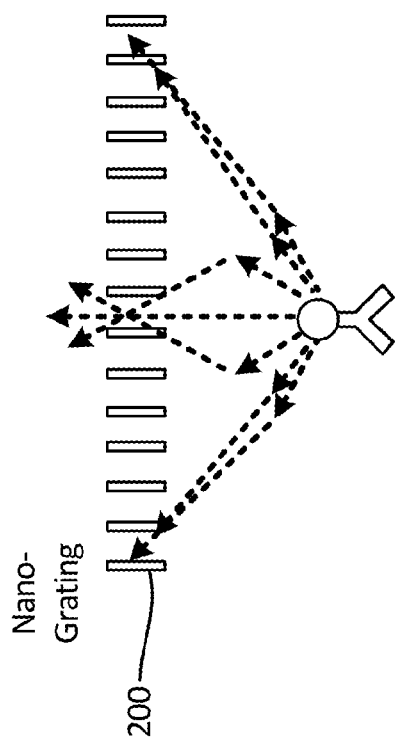
FIG. 17B is a further overview of the nano-gratings, comprising vertical gratings using metal layers.

FIGS. 17A-C depict the result of the use of the cylinder approach to angle sensitivity. In the experimental embodiment, 50% of the light was eliminated when the light enters at 30 degrees, thus theoretically enabling each imager pixel to just receive light from the lens below it. As shown in FIG. 16B, a laser illuminates the sensor surface from between 45 degrees off-axis to zero degrees (or perpendicular). The image is easily seen at +/−15 degrees, but off axis at 30 degrees it is significantly reduced, and at 45 degrees virtually eliminated. The cylinder approach can thus also be used to introduce angle sensitivity to the system.

Figure 18:
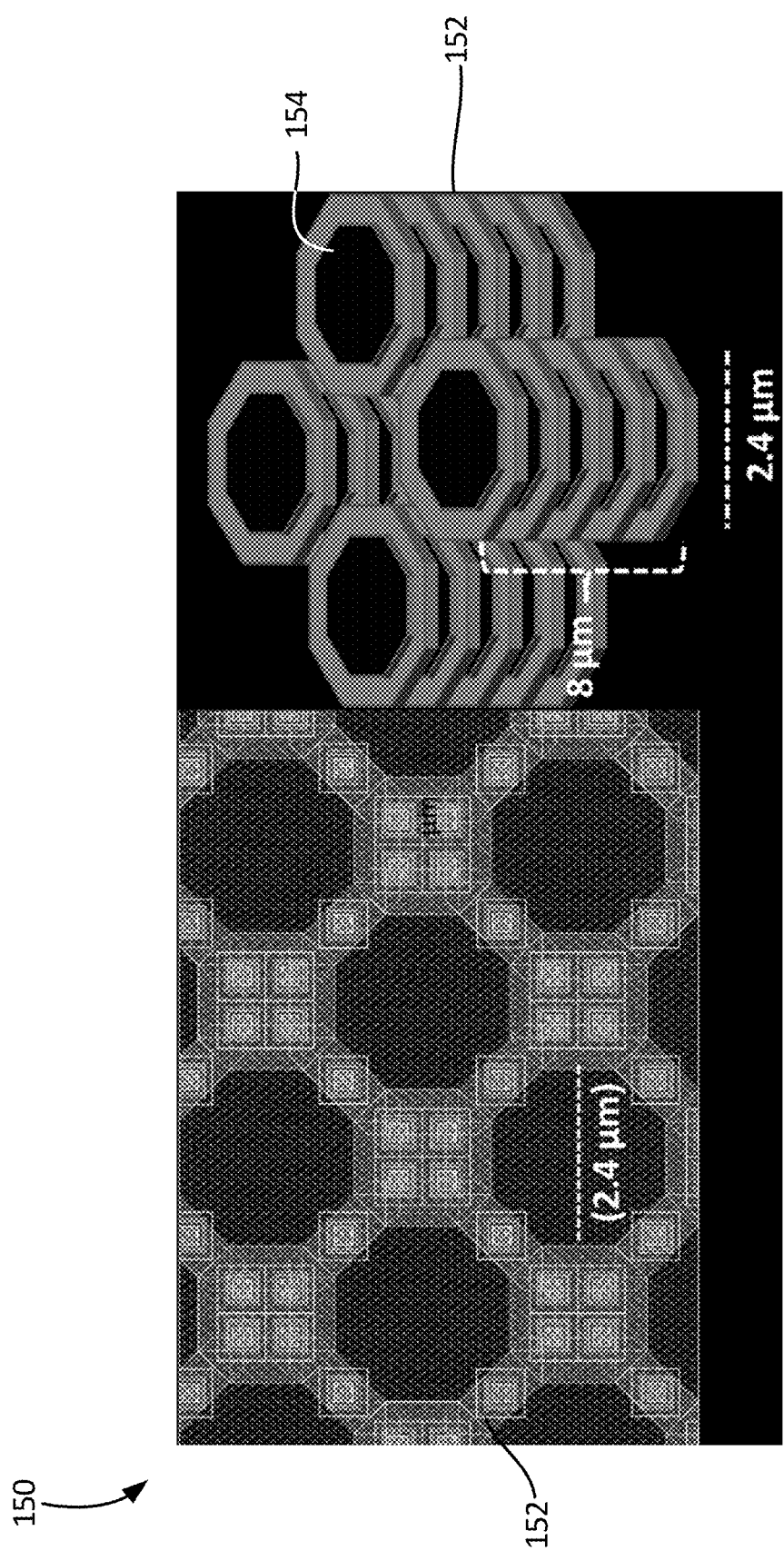
FIG. 18 depicts a top view and a perspective view of a hexogonally-organized angle-sensitive grating, according to one embodiment.
Figure 19:
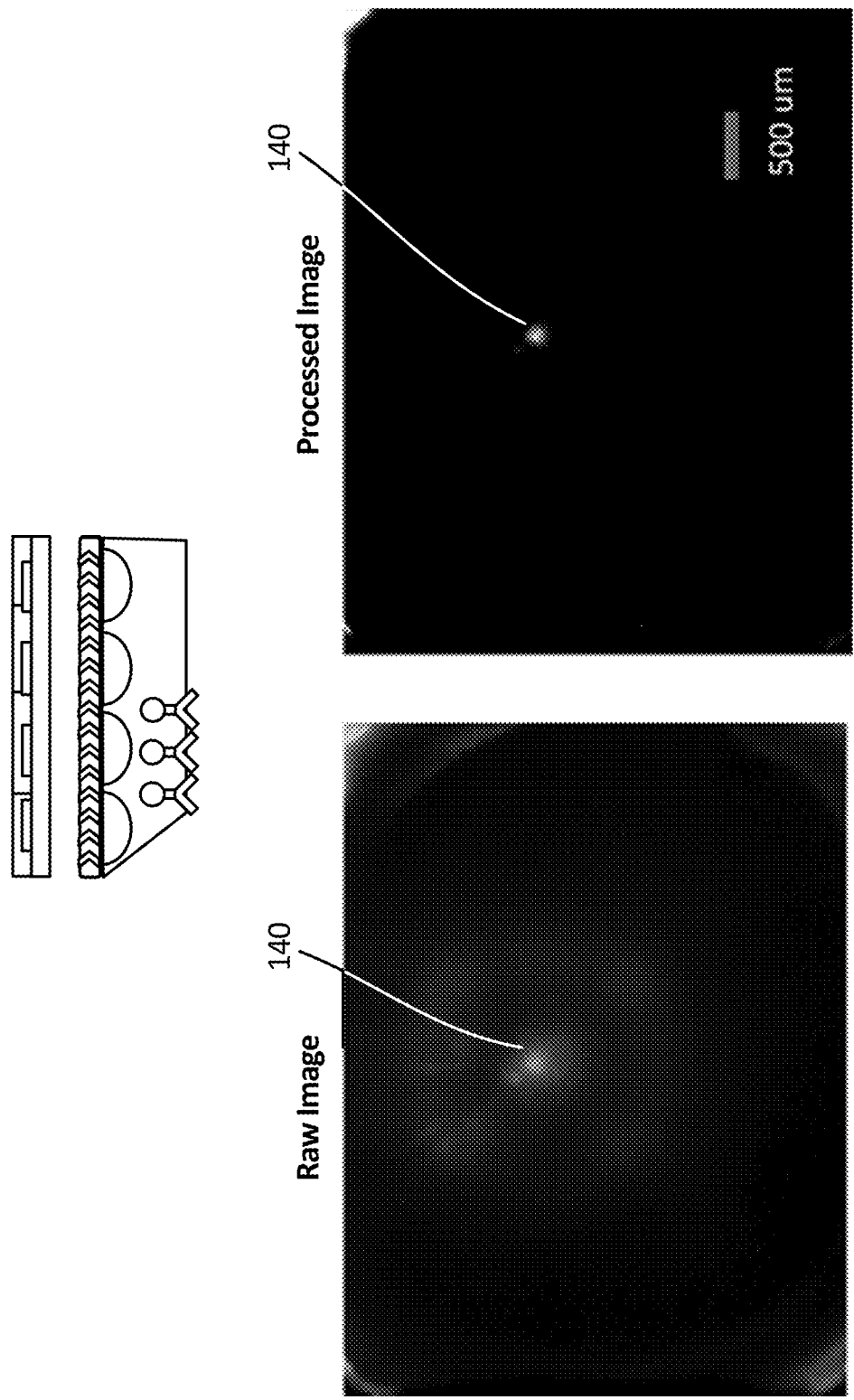
FIG. 19A depicts a raw image taken with a 75 µm fluorescent spot, passed through the microlenses, stencil array, optical filter and onto an integrated charge-coupled device (CCD) sensor, but not an angle selective imager.
FIG. 19B depicts a processed image of FIG. 19A.

FIG. 18 depicts an embodiment of an angle selective grating 150 from the top (left) and from a perspective angle (right). In this embodiment, the openings 154 of the cylinders 152 are 2.4 μm, though other sizes are of course possible. In alternate embodiments the pixels are smaller than the gratings, thus allowing for higher resolution.

FIGS. 19A-B depict raw (FIG. 19A) and processed (FIG. 19B) images of light 140 taken with a 75 μm fluorescent spot, images through the microlenses, stencil array, optical filter and onto an integrated charge-coupled device (CCD) sensor, but not an angle selective imager.

Figure 20:
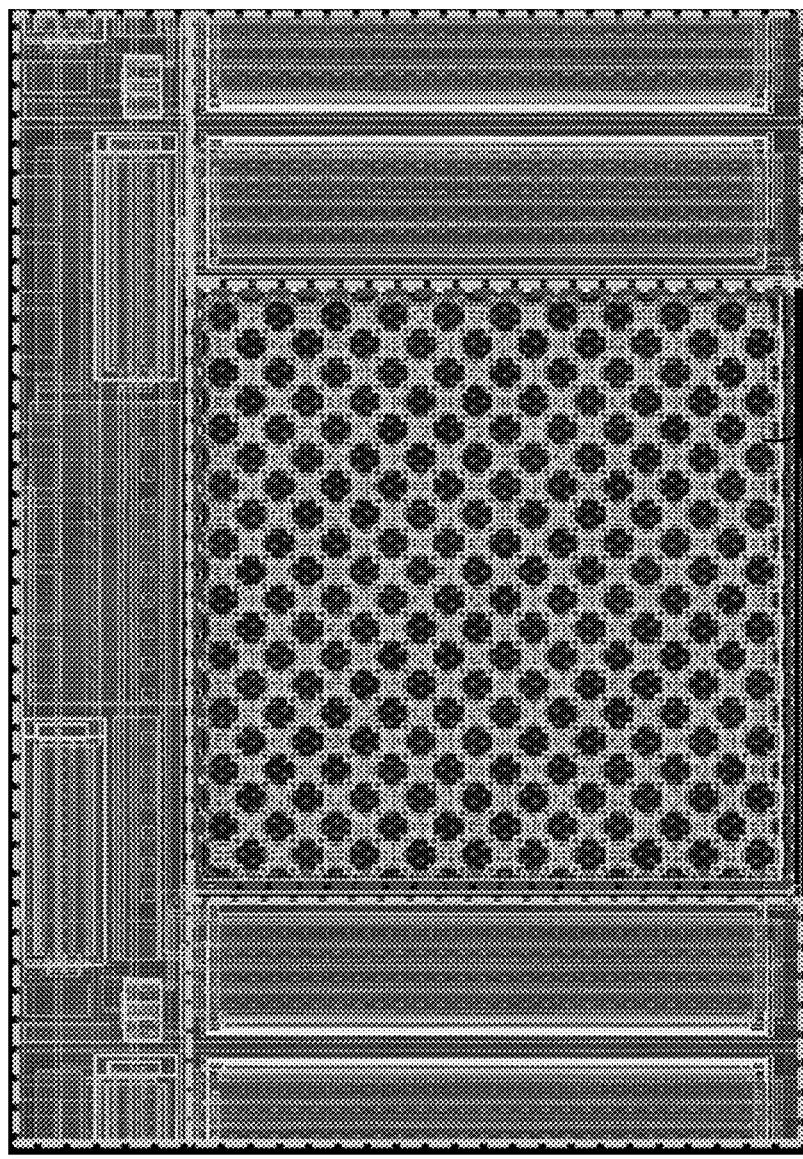
FIG. 20 depicts one exemplary embodiment of a pixel and pixel circuit.

FIG. 20 shows an is a schematic of the pixel 160 showing the photodiode 162 with surrounding circuitry 164; further embodiments can have a greater fill factor with more photodiode and smaller circuitry/transistors; or multiple smaller pixels. The pixels are arranged to spatially correspond with the microlens array, as would be apparent to one of skill in the art.

Figure 21:
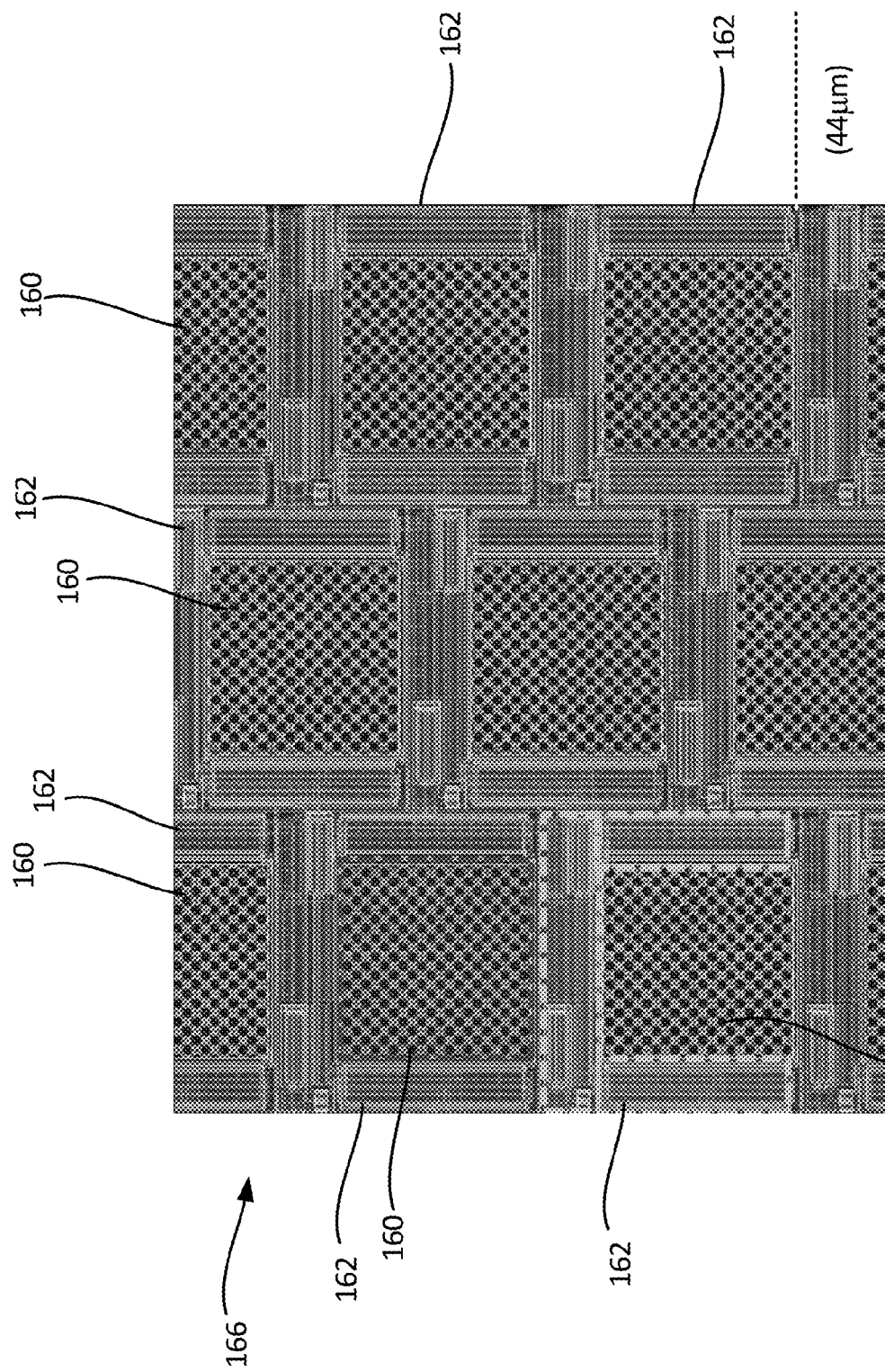
FIG. 21 depicts a hexagonal packed array, according to another embodiment.

FIG. 21 depicts an embodiment of the system comprising a hexagonally packed pixel array 166 according to certain embodiments, comprising a plurality of individual photodiodes 160 and pixel circuitry.

Figure 22B:
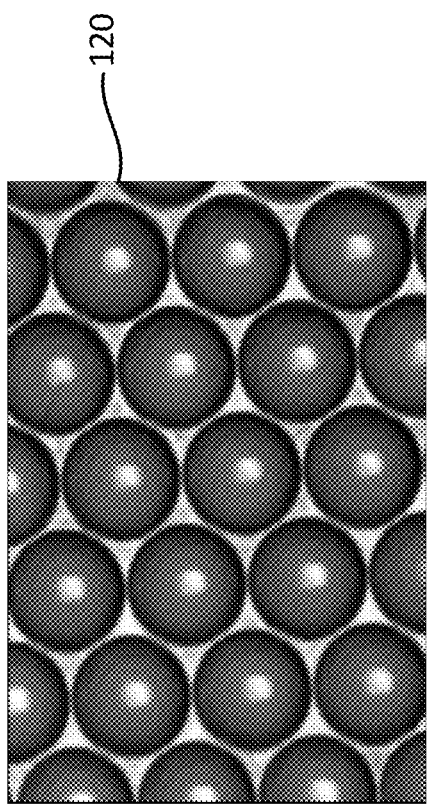
FIG. 22B depicts an exemplary microlens array.
Figure 22A:
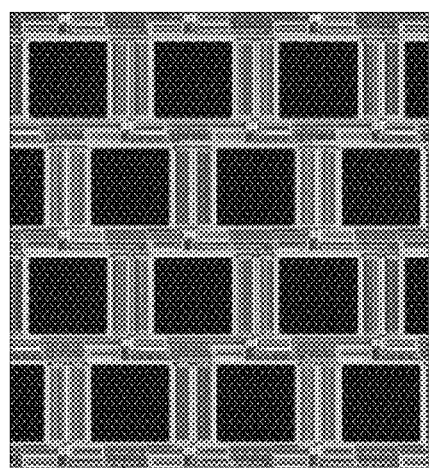
FIG. 22A depicts a top view of a hexagonally-packed pixel array for use with the microlens array of FIG. 22B.

FIGS. 22A-B show an embodiment of the system comprising an alternative hexagonally packed pixel array 168 (FIG. 22A) for μLens array accordingly to further embodiments and the corresponding microlens array 120 (FIG. 22B). One skilled in the art will appreciate that other pixel configurations are possible.

Figure 23:
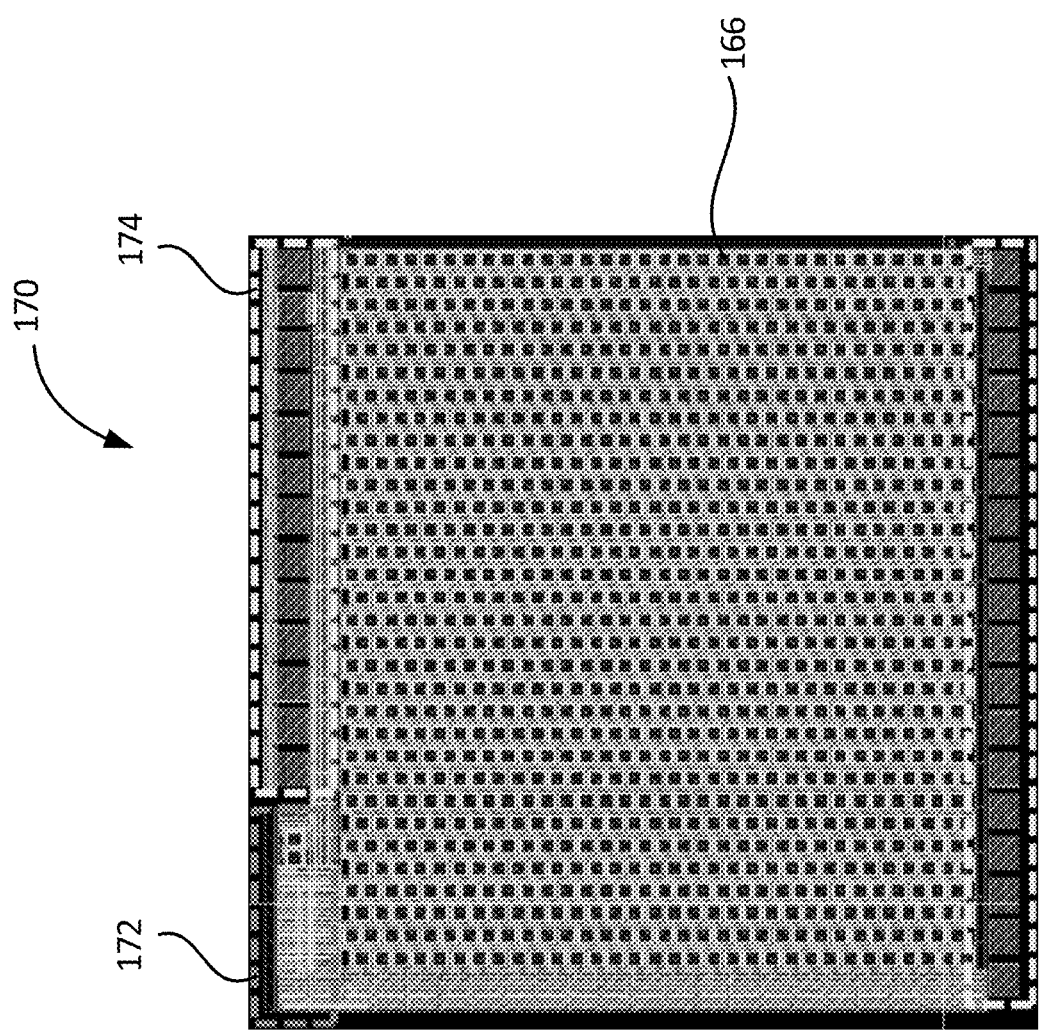
FIG. 23 depicts an exemplary embodiment of a chip layout.

FIG. 23 depicts an alternative the chip 170 layout according to certain embodiments. In these embodiments, the chip 170 comprises a pixel array 166, and further comprises a clock divider 172 and bond pads 174.

Figure 24:
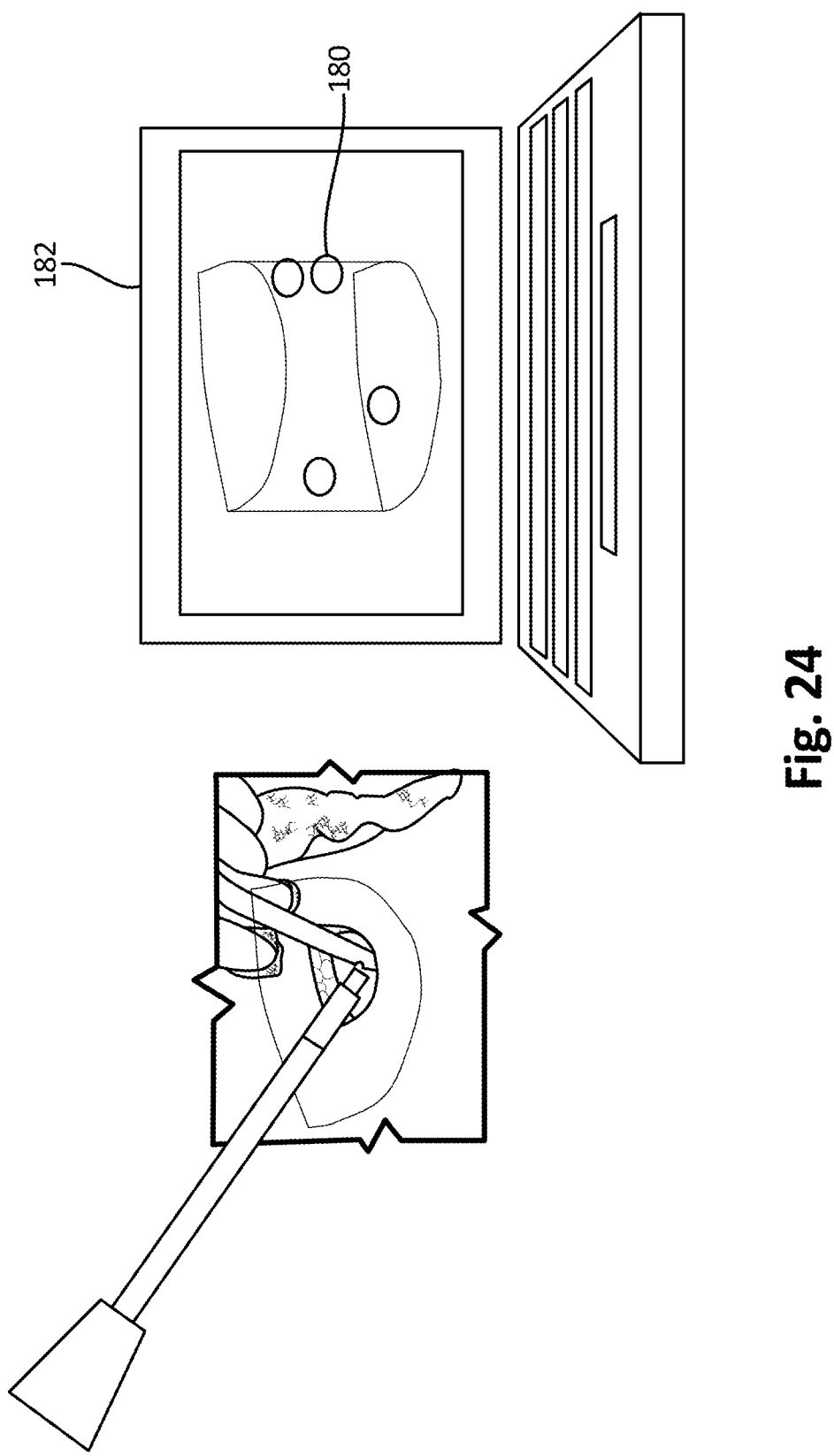
FIG. 24 depicts an exemplary embodiment of a digital processor and visualization component.

As is shown in FIG. 24, in exemplary embodiments, the resulting images 180 can be displayed to the user by way of a commercially-available monitor 182. While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A system for imaging biological material in a patient, comprising:
   a. a fluorescently conjugated molecule capable of binding to the biological material;
   b. a light source;
   c. a fiber optic light guide;
   d. an elongate probe sized for placement inside the cavity of the patient, further comprising at least one substantially planar detection surface, the detection surface further comprising:
      i. an imager;
      ii. a waveguide in luminary communication with the light source; and
      iii. an optical filter; and
   e. a visualization system in electrical communication with the probe;
   wherein the waveguide is capable of emitting light toward the biological material, such that the biological material's emitted fluorescence is received by the imager for display by way of the visualization system.

2. The system of claim 1, further comprising a microlens array.

3. The system of claim 1, wherein the imager further comprises at least one photodiode.

4. The system of claim 3, further comprising a complementary metal oxide semiconductor process.

5. The system of claim 1, further comprising a charge-coupled device process.

6. The system of claim 2, further comprising a waveguide stencil configured to eliminate oblique light from reaching the microlens array.

7. The system of claim 1, wherein the fluorescently conjugated molecule binds biological material selected from the group consisting of: breast cancer cells, prostate cancer cells, cancer cells inside a tumor bed, cancer cells surrounding a tumor bed, disease cells in the microenvironment surrounding a tumor bed.

8. The system of claim 1, wherein optical filter is directly patterned on the imager surface.

9. The system of claim 1, wherein the waveguide further comprises a plurality of optical gratings.

10. The system of claim 1, further comprising a surgical tool, wherein the elongate probe is operationally coupled with the surgical tool.

11. An angle selective imager, comprising:
    a) a light source further comprising a light guide;
    b) an elongate probe sized to be positioned within a body cavity of a patient undergoing surgery, wherein the device is operationally coupled with the light source by way of the light guide, said device further comprising at least one substantially planar detection surface, the detection surface further comprising:
i. an imager further comprising a plurality of pixels; and
ii. a microlens array; and
c) a visualization system in electrical communication with the probe capable of computing and displaying fluorescence wherein the detection surface is adapted to allow light from substantially perpendicular angles from surface to pass through the microlens to the imager, and exclude light incident form other directions.

12. The imager of claim 11, further comprising a micrograting.

13. The imager of claim 11, further comprising a nanograting.

14. The imager of claim 13, further comprising at least one cylinder disposed adjacent to the microlens array adjacent to an imager pixel.

15. The imager of claim 14, further comprising a waveguide, wherein the waveguide is in luminary communication with the light guide.

16. The imager of claim 15, further comprising an optical filter, wherein the waveguide is capable of emitting light toward fluorescently-tagged cells such that emitted fluorescence is passed through the microlens array and nanograting and received by the imager.

17. A modular system for imaging fluorescently tagged disease cells, comprising:
a. at least one imager further comprising a plurality of pixels;
b. at least one waveguide further comprising at least one remote light source, wherein the at least one remote light source is capable of emitting light through the at least one waveguide to fluoresce the tagged cells;
c. at least one microlens array configured to direct light to the imager pixels; wherein the at least one microlens array, imager and waveguide are disposed in a substantially parallel and planar fashion facing the tagged cells so as to transmit light substantially perpendicularly from the tagged cells to the imager by way of the microlens array.

18. The modular system of claim 17, comprising an optical filter.

19. The modular system of claim 18, further comprising an additional modular system disposed to face an alternative plane of tagged disease cells.

20. The modular system of claim 18, wherein the modular system further comprising an angle sensitivity grating.

* * * * *

UNITED STATES PATENT AND TRADEMARK OFFICE
CERTIFICATE OF CORRECTION

PATENT NO. : 9,820,653 B2
APPLICATION NO. : 15/074614
DATED : November 21, 2017
INVENTOR(S) : Anwar et al.

It is certified that error appears in the above-identified patent and that said Letters Patent is hereby corrected as shown below:

On the Title Page

Item (60) should read:
-- Continuation of application No. PCT/US2014/056788, filed on Sep. 22, 2014.
Provisional application No. 61/880,750, filed on Sep. 20, 2013 --

Signed and Sealed this
Twenty-sixth Day of May, 2020

Andrei Iancu
*Director of the United States Patent and Trademark Office*